(12) United States Patent
Chin et al.

(10) Patent No.: US 6,372,742 B1
(45) Date of Patent: Apr. 16, 2002

(54) SUBSTITUTED INDOLE COMPOUNDS AND METHODS OF THEIR USE

(75) Inventors: Allison C. Chin, Stanford; Richard L. Tolman, Los Altos; Mark Q. Nguyen, San Jose; Ryan Holcomb, San Carlos, all of CA (US)

(73) Assignee: Geron Corporation, Menlo Park, CA (US)

( * ) Notice: Subject to any disclaimer, the term of this patent is extended or adjusted under 35 U.S.C. 154(b) by 0 days.

(21) Appl. No.: 09/608,861

(22) Filed: Jun. 30, 2000

Related U.S. Application Data

(60) Provisional application No. 60/142,173, filed on Jul. 1, 1999.

(51) Int. Cl.⁷ ............... A61K 31/4166; A61K 31/5377; C07D 277/04; C07D 417/04
(52) U.S. Cl. ............... 514/236.8; 514/254.02; 514/369; 544/133; 544/367; 548/183
(58) Field of Search ............... 514/236.8, 254.02, 514/369; 544/133, 367; 548/183

(56) References Cited

U.S. PATENT DOCUMENTS

| | | | |
|---|---|---|---|
| 5,554,767 A | 9/1996 | Wang et al. | 548/496 |
| 5,656,638 A | 8/1997 | Gaeta et al. | 514/301 |
| 5,863,936 A | 1/1999 | Gaeta et al. | 514/443 |
| 5,955,616 A | * 9/1999 | Ohtani et al. | 548/183 |

FOREIGN PATENT DOCUMENTS

| | | |
|---|---|---|
| EP | 0 369 344 | 5/1990 |
| EP | 0 587 377 A2 | 3/1994 |
| EP | 0 780 389 A1 | 6/1997 |
| WO | WO 99/65875 | 12/1999 |

OTHER PUBLICATIONS

Eiden, F., et al., "XP–000942756 3–Athenyl–5–Methoxy–Indol Derivate", Archiv Der Pharmazie, 304(7):523–31 (1971).
Eshba, N. H., et al., "XP–002151030 5–(2–Oxo–3–indolinylidene) Thiazolidine–2, 4–dione–1,3–di–Mannich Base Derivatives. Synthesis and Evaluation for Antileukemic Activity", Pharmazie, 40(5):320–2 (1985).
Foglia, T., et al., "Reaction of N,N–Dichlorourethan with Indole and Derivatives", Journal of Organic Chemistry, 33(12):4440 (1968).
Harnden, M.R., et al., "XP–000942720Thiazolinone Analogs of Indomycin with Antiviral and Antibacterial Activity", Journal of Medicinal Chemistry, 21(1):83–7 (1978).
Niigta, K., et al., "XP–002151031 Preparation of Thiazolidinylidene Indoline Derivatives as Cell Migration Inhibitors", Chemical Abstracts, 125(5):1155 (1996).
Ogino, M., et al., "Antitumor Effect of Indomethacin and Telomerase Activity in the Tumor in Colon 26 Bearing CDF1 Mice", Proc. Japan Acad. 73(B):150 (1997).

* cited by examiner

Primary Examiner—T. A. Solola
Assistant Examiner—Sonya N. Wright
(74) Attorney, Agent, or Firm—Geron Corporation

(57) ABSTRACT

5-(3-Isatinylidinyl)thiazolidineones and 3-(thiazolidinon-5-yl)indoles compounds, compositions, and methods of inhibiting telomerase activity in vitro and treatment of telomerase mediated conditions or diseases ex vivo and in vivo are provided. The methods, compounds and compositions of the invention may be employed alone, or in combination with other pharmacologically active agents in the treatment of conditions or diseases mediated by telomerase activity, such as in the treatment of cancer. Also disclosed are novel methods for assaying or screening for inhibitors of telomerase activity.

30 Claims, No Drawings

SUBSTITUTED INDOLE COMPOUNDS AND METHODS OF THEIR USE

CROSS-REFERENCE TO RELATED APPLICATIONS

The application claims priority from U.S. Provisional Application No. 60/142,173, filed Jul. 1, 1999, which is herein incorporated by reference in its entirety.

FIELD OF THE INVENTION

The present invention relates to the synthesis of substituted indole compounds, to pharmaceutical compositions containing the compounds and to the use of the compounds and compositions to inhibit telomerase activity, alone or in combination with other pharmaceutically active agents, in the treatment of telomerase-mediated conditions or diseases, such as cancer.

BACKGROUND OF THE INVENTION

Telomerase catalyzes the synthesis of telomeres. Telomeres are characteristic tandem repeats (TTAGGG in mammals) found at the ends of most eukaryotic chromosomes, that may be 15–25 kilobases long in human germline cells. With each cell division, about 60–100 bases are lost from the ends of the chromosomes, and as the telomeres shorten, cells eventually reach crisis and apotosis is triggered. See Harley et al., (1991) Mutation Res. 256: 271–282. Telomerase acts to maintain the telomere length just above the crisis level, and are thus responsible for chromosome stability and are involved in the regulation of the cell cycle.

Telomerase is a ribonucleoprotein reverse transcriptase that contains its own RNA template for the synthesis of telomeric DNA. See Blackburn, (1992) Annu. Rev. Biochem., 61: 113–129. Telomerase is present in stem and germline cells of normal tissues, and at much higher levels in over 85% of tumors (Kim, et al., (1994) Science, 266: 2011–2014). Thus, drugs targeted towards telomerase potentially will have a high selectivity for tumor over healthy tissues. Consequently, telomerase inhibition has been proposed as a new approach to cancer therapy.

The inhibition of telomerase activity by antisense strategies directed towards the telomerase RNA component, for example peptide nucleic acids (Norton et al., (1996) Nature Biotech. 14: 615–619) and phosphorothioate oligonucleotides has been reported. Since telomerase is a reverse transcriptase, the use of inhibitors of reverse transcriptases, such as AZT, and other nucleosides has also been reported. Telomerase inhibition by cisplatin, possibly due to crosslinking of the telomeric repeat sequences, is also known (Burger et al., (1997) Eur. J. Cancer 33: 638–644). Methods for detecting telomerase activity, as well as for identifying compounds that regulate or affect telomerase activity, together with methods for therapy and diagnosis of cellular senescence and immortalization by controlling telomere length and telomerase activity, have also been described. See, Feng, et al., 1995, Science, 269:1236–1241; Kim, et al., 1994, Science, 266:2011–2014; PCT patent publication No. 93/23572, published Nov. 25, 1993; and U.S. Pat. Nos. 5,760,062, 5,767,278, 5,770,613 and 5,863,936.

U.S. Pat. No. 5,656,638 lists compounds that may have anti-telomerase activity. U.S. Pat. No. 5,556,874 discloses substituted 2-thioindoles are inhibitors of the epidermal growth receptor tyrosine kinase. In addition, 2-oxindole-1-carboxamides are disclosed to be inhibitors of cyclooxygenase and lipoxygenase in U.S. Pat. Nos. 4,569,942 and 4,556,672, and as being capable of inhibiting the biosynthesis of interleukin-1 in U.S. Pat. No. 4,861,794.

The synthesis of some isatinylidineacetic acid derivatives is described by Autrey and Tahk (1967) Tetrahedron 23: 901–917, and the structure elucidation of indolmycin, a antibiotic, is described by von Wittenau and Els (1963) J. Am. Chem. Soc. 86: 3425–3431.

The identification of compounds that inhibit telomerase activity provides important benefits to efforts at treating human disease. Compounds that inhibit telomerase activity can be used to treat telomerase-mediated disorders, such as cancer, since cancer cells express telomerase activity and normal human somatic cells do not possess telomerase activity at biologically relevant levels (i.e., at levels sufficient to maintain telomere length over many cell divisions). Unfortunately, few such compounds, especially compounds with high potency or activity and compounds that are orally bioavailable, have been identified and characterized. Hence, there remains a need for compounds that act as telomerase inhibitors that have relatively high potency or activity and that are orally bioavailable, and for compositions and methods for treating cancer and other diseases in which telomerase activity is present abnormally.

SUMMARY OF THE INVENTION

In one aspect, the invention relates to the synthesis and characterization of thiazolidinedione indole and 5-(3-isatinylidenyl)-2,4-thiazolidinedione compounds and the use of these compounds as inhibitors of the telomerase enzyme. Thus, in certain aspects, the present invention provides methods of inhibiting telomerase by contacting telomerase with the compounds described herein. In particular embodiments, the telomerase to be inhibited is a mammalian telomerase, such as a human telomerase. A related aspect of the present invention is the discovery that thiazolidinedione indole and 5-(3-isatinylidenyl)-2,4-thiazolidinedione inhibit the proliferation of cells that have telomerase activity, such as many cancer cells. Thus, this aspect of the present invention provides methods of inhibiting telomerase activity in a cell, such as a cancer cell. Further, the invention provides methods of inhibiting telomerase activity in a subject (for example a human or other mammalian subject) suffering from a telomerase-mediated condition or disease, comprising administering to the patient a therapeutically effective amount of a telomerase inhibiting thiazolidinedione indole or 5-(3-isatinylidenyl)-2,4-thiazolidinedione compound, or a pharmaceutically acceptable salt thereof. Thus, the compounds are useful as inhibitors of telomerase and as antitumor agents.

More particularly, the invention comprises compounds, and their pharmaceutically acceptable salts, of formula (I):

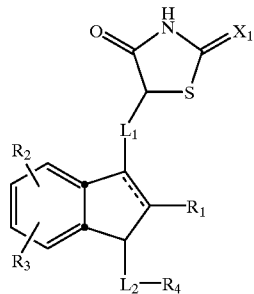

(I)

wherein $X_1$ is chosen from O, S, $CH_2$, or $NR_5$ where $R_5$ is H, lower alkyl or aryl;

$L_1$ is a direct single bond, direct double bond, —$CH_2$—, or —CH=;

⸾ is a single or a double bond;

$R_1$ is selected from the group consisting of H, $OR_5$, $SR_5$, $CR_6R_7R_8$, and oxo only when ⸾ is a single, wherein $R_6$, $R_7$, and $R_8$ are independently selected from H, OH, lower alkyl, aryl, or heteroaryl;

$R_2$ and $R_3$ are independently selected from the group consisting of H, OH, halogen, mercapto, nitro, cyano, trifluoromethyl, lower alkyl, lower alkoxy, aryloxy, $NR_9R_{10}$, $SO_2NR_9R_{10}$, $OCHR_9R_{10}$, $COR_9$, $CO_2R_9$, $NHCONHR_9$, $CONHR_9$, $NHCOR_9$, aryl, and heteroaryl wherein $R_9$ and $R_{10}$ are independently selected from the group consisting of hydrogen, lower alkyl, aryl, and heteroaryl, and $R_2$ and $R_3$ further represent replacement in the ring of ring methine (—CH=) atoms with aza (—N=) atoms;

$L_2$ is a direct single bond or a linking group having from 1 to 3 atoms independently selected from unsubstituted or substituted carbon, N, O or S; and $R_4$ is H, lower alkyl, alkaryl, aryl, or heteroaryl.

In another aspect, the invention relates to isatin compounds comprising formula (II):

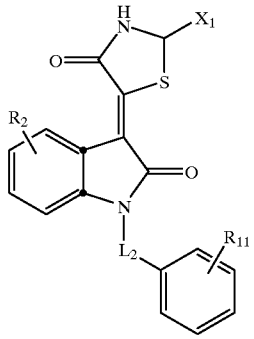

(II)

wherein $X_1$ is O or S;

$R_2$ is H, OH, halogen, lower alkyl, aryl, or heteroaryl;

$L_2$ is a direct bond, $CH_2$, or $SO_2$; and $R_{11}$ is H, halogen or lower alkoxy;

or a pharmaceutically acceptable salt thereof.

The new compounds of the invention have many valuable uses as inhibitors of deleterious telomerase activity, such as, for example, in the treatment of cancer in mammals, such as humans. The pharmaceutical compositions of this invention can be employed in treatment regimens in which cancer cells are killed, in vivo, or can be used to kill cancer cells ex vivo. Thus, this invention provides therapeutic compounds and compositions for treating cancer, and methods for treating cancer and other telomerase-mediated conditions or diseases in humans and other mammals (e.g., cows, horses, sheep, steer, pigs and animals of veterinary interest such as cats and dogs).

DETAILED DESCRIPTION

I. Definitions

Unless otherwise defined below, the terms used herein have their normally accepted scientific meanings. Definition of standard chemistry terms may be found in reference works, including Carey and Sundberg (1992) "Advanced Organic Chemistry $3^{rd}$ Ed." Vols. A and B, Plenum Press, New York.

The term "indole" or "indole derivative" as used herein refers to compounds of the general formula:

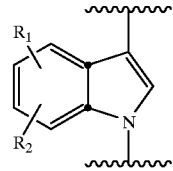

The term "isatin" or "isatin derivative" as used herein refers to compounds of the general formula:

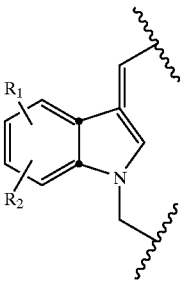

The term "thiazolidineone" or "thiazolidineone derivative" as used herein refers to compounds of the general formula:

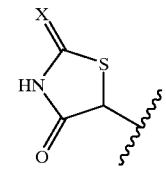

wherein X is O or S. When X is O, the derivatives are thiazolidinedione derivatives. When X is S, the derivatives are the thiazolidinonethione derivatives also known as rhodanines.

The term "alkyl" as used herein refers to a straight, branched, or cyclic hydrocarbon chain fragment or radical containing between about one and about twenty carbon atoms, more preferably between about one and about ten carbon atoms (e.g., methyl, ethyl, n-propyl, iso-propyl, cyclopropyl, n-butyl, iso-butyl, tert-butyl, cyclobutyl, adamantyl, noradamantyl and the like). Straight, branched, or cyclic hydrocarbon chains having eight or fewer carbon atoms will also be referred to herein as "loweralkyl". The hydrocarbon chains may further include one or more degrees of unsaturation, i.e., one or more double or triple bonds (e.g., vinyl, propargyl, allyl, 2-buten-1-yl, 2-cyclopenten-1-yl, 1,3-cyclohexadien-1-yl, 3-cyclohexen-1-yl and the like). Alkyl groups containing double bonds such as just described will also be referred to herein as "alkenes". Similarly, alkyl groups having triple bonds will also be referred to herein as "alkynes". However, as used in context with respect to cyclic alkyl groups, the combinations of double and/or triple bonds do not include those bonding arrangements that render the cyclic hydrocarbon chain aromatic.

The term "oxo" means a doubly bonded oxygen.

In addition, the term "alkyl" as used herein further includes one or more substitutions at one or more carbon atoms of the hydrocarbon fragment or radical. Such substitutions include, but are not limited to: aryl; heterocycle; halogen (to form, e.g., trifluoromethyl, ——$CF_3$); nitro (——$NO_2$); cyano (——CN); hydroxyl (also referred to herein as "hydroxy"), alkoxyl (also referred herein as alkoxy) or aryloxyl (also referred to herein as "aryloxy", ——OR); thio or mercapto, alkyl, or arylthio (——SR); amino, alkylamino, arylamino, dialkyl- or diarylamino, or arylalkylamino (——NRR'); aminocarbonyl, alkylaminocarbonyl, arylaminocarbonyl, dialkylaminocarbonyl, diarylaminocarbonyl or arylalkylaminocarbonyl (——C(O)NRR'); carboxyl, or alkyl- orarylloxycarbonyl (——C(O)OR); carboxaldehyde, or aryl- or alkylcarbonyl (——C(O)R); iminyl, aryl- or alkyliminyl (——C(=NR)R'); sulfo (——$SO_2$OR); alkyl- or arylsulfonyl (——$SO_2$R); carbamido (——HNC(=O)NRR'); orthiocarbamido (——HNC(=S)NRR'); where R and R' independently are hydrogen, aryl or alkyl as defined herein. Substituents including heterocyclic groups (i.e., heterocycle, heteroaryl, and heteroaralkyl) are defined by analogy to the above-described terms. For example, the term "heterocycleoxy" refers to the group ——OR, where R is heterocycle as defined below.

The term "methylene" refers to the group —$CH_2$——.

The term "methine" refers to a methylene group for which one hydrogen atom has been replaced by a substituent as described above. The term "methine" can also refer to a methylene group for which one hydrogen atom is replaced by bond to form an $sp^2$-hybridized carbon center (i.e., >C=O).

The term "halo" or "halogen" as used herein refers to the substituents fluoro, bromo, chloro, and iodo.

The term "carbonyl" as used herein refers to the functional group ——C(O)——. However, it will be appreciated that this group may be replaced with well-known groups that have similar electronic and/or steric character, such as thiocarbonyl (——C(S)——); sulfinyl (——S(O)——); sulfonyl (——$SO_2$——)phosphonyl (——$PO_2$——), and methine. Other carbonyl equivalents will be familiar to those having skill in the medicinal and organic chemical arts.

The term "aryl" as used herein refers to cyclic aromatic hydrocarbon chains having twenty or fewer carbon atoms, e.g., phenyl, naphthyl, biphenyl and anthryl. One or more carbon atoms of the aryl group may also be substituted with, e.g.: alkyl; aryl; heterocycle; halogen; nitro; cyano; hydroxyl, alkoxyl or aryloxyl; thio or mercapto, alkyl-, or arylthio; amino, alkylamino, arylamino, dialkyl-, diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; carboxaldehyde, or aryl- or alkylcarbonyl; iminyl, or aryl- or alkyliminyl; sulfo; alkyl- or arylsulfonyl; hydroximinyl, or aryl- or alkoximinyl; carbamido; or thiocarbamido. In addition, two or more alkyl or heteroalkyl substituents of an aryl group may be combined to form fused aryl-alkyl or aryl-heteroalkyl ring systems (e.g., tetrahydronaphthyl). Substituents including heterocyclic groups (e.g., heterocycleoxy, heteroaryloxy, and heteroaralkylthio) are defined by analogy to the above-described terms.

The term "aralkyl" as used herein refers to an aryl group that is joined to a parent structure by an alkyl group as described above, e.g., benzyl, α-methylbenzyl, phenethyl, and the like.

The term "heterocycle" as used herein refers to a cyclic alkyl group or aryl group as defined above in which one or more carbon atoms have been replaced by a non-carbon atom, especially nitrogen, oxygen, or sulfur. Non-aromatic heterocycles will also be referred to herein as "cyclic heteroalkyl". Aromatic heterocycles are also referred to herein as "heteroaryl". For example, such groups include furyl, tetrahydrofuryl, pyrrolyl, pyrrolidinyl, thienyl, tetrahydrothienyl, oxazolyl, isoxazolyl, triazolyl, thiazolyl, isothiazolyl, pyrazolyl, pyrazolidinyl, oxadiazolyl, thiadiazolyl, imidazolyl, imidazolinyl, pyridyl, pyridazinyl, triazinyl, piperidinyl, morpholinyl, thiomorpholinyl, pyrazinyl, piperazinyl, pyrimidinyl, naphthyridinyl, benzofuranyl, benzothienyl, indolyl, indolinyl, indolizinyl, indazolyl, quinolizinyl, quinolinyl, isoquinolinyl, cinnolinyl, phthalazinyl, quinazolinyl, quinoxalinyl, pteridinyl, quinuclidinyl, carbazolyl, acridiniyl, phenazinyl, phenothiazinyl, phenoxazinyl, purinyl, benzimidazolyl, benzthiazolyl, and benzoxazolyl.

The above heterocyclic groups may further include one or more substituents at one or more carbon and/or non-carbon atoms of the heteroaryl group, e.g.: alkyl; aryl; heterocycle; halogen; nitro; cyano; hydroxyl, alkoxyl or aryloxyl; thio or mercapto, alkyl- or arylthio; amino, alkyl-, aryl-, dialkyl-diaryl-, or arylalkylamino; aminocarbonyl, alkylaminocarbonyl, arylaminocarbonyl, dialkylaminocarbonyl, diarylaminocarbonyl or arylalkylaminocarbonyl; carboxyl, or alkyl- or aryloxycarbonyl; carboxaldehyde, or aryl- or alkylcarbonyl; iminyl, or aryl- or alkyliminyl; sulfo; alkyl- or arylsulfonyl; hydroximinyl, or aryl- or alkoximinyl; carbamido; or thiocarbamido. In addition, two or more alkyl substituents may be combined to form fused heterocycle-alkyl or heterocycle-aryl ring systems. Substituents including heterocyclic groups (e.g., heterocycleoxy, heteroaryloxy, and heteroaralkylthio) are defined by analogy to the above-described terms.

The term "heterocyclealkyl" refers to a heterocycle group that is joined to a parent structure by one or more alkyl groups as described above, e.g., 2-piperidylmethyl, and the like. The term "heteroaralkyl" as used herein refers to a heteroaryl group that is joined to a parent structure by one or more alkyl groups as described above, e.g., 2-thienylmethyl, and the like.

The compounds of the present invention may be used to inhibit or reduce telomerase enzyme activity and/or proliferation of cells having telomerase activity. In these contexts, inhibition and reduction of the enzyme or cell proliferation refers to a lower level of the measured activity relative to a control experiment in which the enzyme or cells are not treated with the test compound. In particular embodiments, the inhibition or reduction in the measured activity is at least a 10% reduction or inhibition. One of skill in the art will appreciate that reduction or inhibition of the measured activity of at least 20%, 50%, 75%, 90% or 100% may be preferred for particular applications.

II. Telomerase Inhibitors

As noted above, the immortalization of cells involves inter alia the activation of telomerase. More specifically, the connection between telomerase activity and the ability of many tumor cell lines, including skin, connective tissue, adipose, breast, lung, stomach, pancreas, ovary, cervix, uterus, kidney, bladder, colon, prostate, central nervous system (CNS), retina and blood tumor cell lines, to remain immortal has been demonstrated by analysis of telomerase activity (Kim, et al.). This analysis, supplemented by data that indicates that the shortening of telomere length can provide the signal for replicative senescence in normal cells (see WO 93/23572), demonstrates that inhibition of telomerase activity can be an effective anti-cancer therapy. By "inhibition" is simply meant a reagent, drug or chemical which is able to decrease the activity of the telomerase enzyme in vitro or in vivo. Such inhibitors can be readily identified using standard screening protocols in which a cellular extract or other preparation having telomerase activity is placed in contact with a potential inhibitor, and the level of telomerase activity measured in the presence or absence of the inhibitor, or in the presence of varying amounts of inhibitor. In this way, not only can useful inhibitors be identified, but the optimum level of such an inhibitor may be determined in vitro for further testing in vivo.

In a related aspect, the invention proves a method for inhibiting the ability of a cell to proliferate or replicate. In this method, one or more of the substituted indole and isatin compounds of the invention, that are capable of inhibiting telomerase enzyme activity, are provided during cell replication. As explained above, telomeres play a critical role in allowing the end of the linear chromosomal DNA to be replicated completely without the loss of terminal bases at the 5'-end of each strand. Immortal cells and rapidly proliferating cells use telomerase to add telomeric DNA repeats to chromosomal ends. Inhibition of telomerase will result in the proliferating cells not being able to add telomeric repeats and they will eventually stop dividing. As will be evident to those of ordinary skill in the art, this method for inhibiting the ability of a cell to proliferate is useful for the treatment of a condition associated with an increased rate of proliferation of a cell, such as in cancer (by inhibiting telomerase enzyme activity in malignant cells), and hematopoiesis (by inhibiting telomerase activity in hematopoietic stem cells), for example.

Thus, in one aspect, the present invention provides compositions and compounds for the prevention or treatment of many types of malignancies. In particular, the compounds of the present invention can provide general method of treating many, if not most, malignancies, as demonstrated by the highly varied human tumor cell lines and tumors having telomerase activity. Further, the substituted indole and isatin compounds of the present invention are telomerase specific, i.e. they can discriminate between malignant and normal cells to a high degree, avoiding many of the deleterious side-effects present with most current chemotherapeutic regimes which rely on agents that kill dividing cells indiscriminately.

In another aspect, the present invention provides new compounds, pharmaceutical compositions and methods relating to the new compounds, or their pharmaceutically acceptable salts, for inhibiting a telomerase enzyme. Typically, these methods comprise contacting the telomerase enzyme with a compound, or its pharmaceutically acceptable salt, having the formula (I).

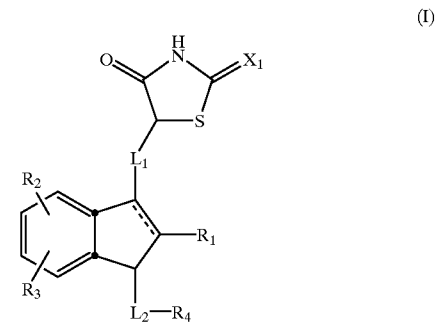

(I)

wherein $X_1$ is chosen from O, S, $CH_2$, or $NR_5$ where $R_5$ is H, lower alkyl or aryl;

$L_1$ is a direct single bond, direct double bond, —$CH_2$—, or —CH=;

⟋ is a single or a double bond;

$R_1$ is selected from the group consisting of H, $OR_5$, $SR_5$, $CR_6R_7R_8$, and oxo only when ⟋ is a single, wherein $R_6$, $R_7$, and $R_8$ are independently selected from H, OH, lower alkyl, aryl, or heteroaryl;

$R_2$ and $R_3$ are independently selected from the group consisting of H, OH, halogen, mercapto, nitro, cyano, trifluromethyl, lower alkyl, lower alkoxy, aryloxy, $NR_9R_{10}$, $SO_2NR_9R_{10}$, $OCHR_9R_{10}$, $COR_9$, $CO_2R_9$, $NHCONHR_9$, $CONHR_9$, $NHCOR_9$, aryl, and heteroaryl wherein $R_9$ and $R_{10}$ are independently selected from the group consisting of hydrogen, lower alkyl, aryl, and heteroaryl, and $R_2$ and $R_3$ further represent replacement in the ring of ring methine (—CH=) atoms with aza (—N=) atoms;

$L_2$ is a direct single bond or a linking group having from 1 to 3 atoms independently selected from unsubstituted or substituted carbon, N, O or S; and $R_4$ is H, lower alkyl, alkaryl, aryl, or heteroaryl.

In the compounds of formula I, $R_2$, $R_3$, and $R_4$ may be aryl to form, for example, a phenyl moiety. Alternatively, $R_2$, $R_3$, and $R_4$ may be heteroaryl, such as, for example, pyridinyl, pyrimidinyl, thiophenyl, and the like. In certain embodiments, at least one of $R_2$, $R_3$, or $R_4$ is phenyl. In other embodiments, when ⟋ is a double bond, $R_1$ can not be oxo. In yet other embodiments, at least one of $R_2$ and $R_3$ is other than hydrogen, such as, for example, when at least one of $R_2$ and $R_3$ is halo, most preferably both $R_2$ and $R_3$ are halo to form a dihalo-substituted indole moiety.

As noted above, $L_2$ is a linking group that may be a direct bond, or may be a 1 to 3 atom linking group wherein the atoms of the linking group independently selected from unsubstituted or substituted carbon, N, O or S. Representative linking groups useful in the compounds of the invention include, for example —O—, —S—, —NH—, —$CH_2$—, —$OCH_2$—, —OC(O)—, —$CO_2$—, —NHC(O)—, —C(O)NH—, —OC(O)$CH_2$—, —OC(O)NH—, and —NHC(O)NH—.

In certain embodiments, the new compounds of the present invention have the general structure shown as formula II below:

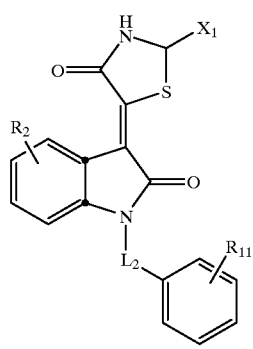

(II)

wherein $X_1$ is O or S;

$R_2$ is H, OH, halogen, lower alkyl, aryl, or heteroaryl;

$L_2$ is a direct bond, $CH_2$, or $SO_2$; and $R_{11}$ is H, halogen or lower alkoxy;

or a pharmaceutically acceptable salt thereof.

The compounds may be in the form of pharmaceutically acceptable salts or esters, or may be modified by appending one or more appropriate functionalities to enhance selected biological properties. Such modifications are known in the art and include those which increase biological penetration into a given biological system, increase oral bioavailability, increase solubility to allow administration by injection, and the like.

III. Synthesis of Telomerase Inhibitors

The compounds of the present invention can be synthesized using techniques and materials known to those of skill in the art, such as described, for example, in March, ADVANCED ORGANIC CHEMISTRY 4th Ed., (Wiley 1992); Carey and Sundberg, ADVANCED ORGANIC CHEMISTRY 3rd Ed., Vols. A and B (Plenum 1992), and Green and Wuts, PROTECTIVE GROUPS IN ORGANIC SYNTHESIS 2nd Ed. (Wiley 1991). Starting materials for the compounds of the invention may be obtained using standard techniques and commercially available precursor materials, such as those available from Aldrich Chemical Co. (Milwaukee, Wis.), Sigma Chemical Co. (St. Louis, Mo.), Lancaster Synthesis (Windham, N.H.), Apin Chemicals, Ltd. (New Brunswick, N.J.), Ryan Scientific (Columbia, S.C.), Maybridge (Cornwall, England), Arcos (Pittsburgh, Pa.), and Trans World Chemicals (Rockville, Md.).

The procedures described herein for synthesizing the compounds of the invention may include one or more steps of protection and deprotection (e.g., the formation and removal of acetal groups). In addition, the synthetic procedures disclosed below can include various purifications, such as column chromatography, flash chromatography, thin-layer chromatography (TLC), recrystallization, distillation, high-pressure liquid chromatography (HPLC) and the like. Also, various techniques well known in the chemical arts for the identification and quantification of chemical reaction products, such as proton and carbon-13 nuclear magnetic resonance ($^1$H and $^{13}$C NMR), infrared and ultraviolet spectroscopy (IR and UV), X-ray crystallography, elemental analysis (EA), HPLC and mass spectroscopy (MS) can be used as well. Methods of protection and deprotection, purification, identification and quantification are well known in the chemical arts.

Compounds of the class represented by formulas I and II can be synthesized using General Procedure 1 and General Procedure 2 described in detail in the Examples below. Detailed protocols from which the individual compounds described above can be synthesized are also provided in the Examples.

In general, the indole containing compounds of formula (I) can be prepared by the process described in the following reaction Scheme 1.

SCHEME 1

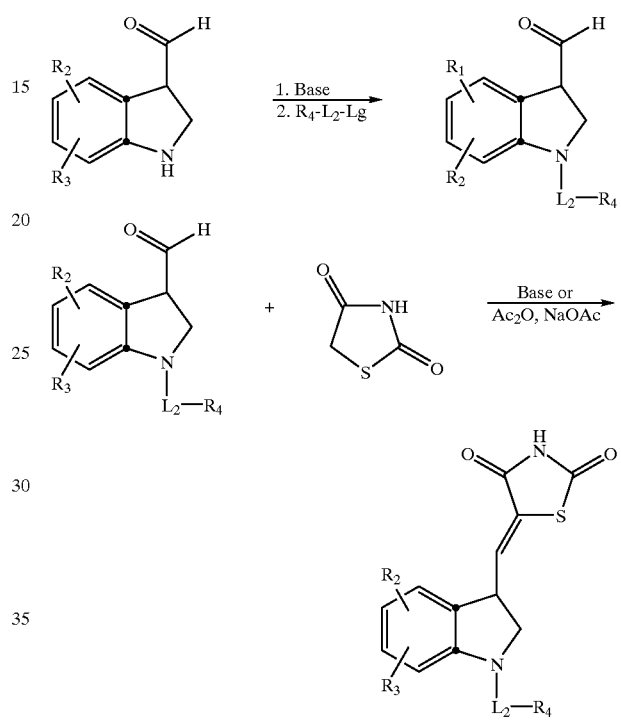

In scheme I, $R_2$—$R_4$ are designated in Formula (I). Indole-3-carbaldehyde, having the desired $R_2$ and $R_3$ substituents, is reacted with $R_4$—$L_4$ having a leaving group (Lg) in the presence of a base, such as potassium carbonate, optionally in the presence of a solvent. Appropriate solvents are those which will at least partially dissolve one or all of the reactants and will not adversely interact with either the reactants or the product. Suitable solvents are aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, alcohols such as methanol, ethanol, n-propanol, isopropanol, n-butanol and tert-butanol, and also dimethyl sulfoxide (DMSO), dimethylformamide (DMF) and water, especially preferably DMSO, DMF, acetonitrile, and toluene. Mixtures of these can also be used. The leaving group on $R_4$—$L_4$ is appropriately chosen for the reaction conditions, and includes halogen or sulfonate groups, preferably chlorine, bromine, iodine, mesylate, tosylate or triflate. Suitable bases are, generally, inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal hydrides and alkaline earth metal hydrides such as lithium hydride, sodium hydride, potassium hydride and calcium hydride, alkali metal amides such as lithium amide, sodium amide and potassium amide, alkali metal carbonates and alkaline earth metal carbonates such as lithium carbonate and calcium carbonate, and also alkali metal hydrogen carbonates such as sodium hydrogen carbonate, organometal compounds, in particular alkali metal alkyls such as methyllithium, butyllithium and phenyllithium, alkylmagnesium halides such as methylmagnesium chloride, and alkali metal alkoxides and alkaline earth metal alkoxides such as sodium methoxide, sodium ethoxide, potassium ethoxide, potassium tert-butoxide and dimethoxymagnesium, furthermore organic bases, eg. tertiary amines such as trimethylamine, triethylamine, triisopropylamine and N-methylpiperidine, pyridine, substituted pyridines such as collidine, lutidine and 4-dimethylaminopyridine, and also bicyclic amines. Sodium hydride, potassium hydroxide, potassium carbonate and triethylamine are especially preferred.

The resulting N-alkylated indole product is dissolved in a solvent and slowly added to a solution comprising approximately an 1.5 molar equivalent amount of thiazolidinedione. The reaction mixture is then heated to an elevated temperature, preferably to near the boiling point of the solvent, until the reaction is complete. The solvent is preferably a polar aprotic solvent, such as DMF, dimethylacetamide, N-methylpyrrolidone, DMSO, methanol, ethanol, propanol, and the like. A preferred solvent is DMF. A wide variety of basic agents can be used in the condensation of thiazolidinedione with the indolealdehyde. However, preferred basic agents are amines, such as trimethylamine, triethylamine, tributylamine, N-methylmorpholine, piperidine, N-methylpiperidine, pyridine and 4-(N,N-dimethylamino)pyridine, with a particularly preferred basic agent being 4-(N,N-dimethylamino) pyridine. Reaction times of about 30 minutes to about 72 hours are common. At the end of the reaction, the volatile components are removed under reduce pressure. The reaction mixture can be optionally acidified before workup. The product is precipitated and recovered such as by filtration. The product can then be washed, dried and further purified by standard methods such as recrystallization.

The double bonds in the compounds of Scheme 1 may be reduced to a single bond by hydrogenation. Typically, hydrogenation is carried out using a noble metal catalyst, such as palladium, platinum, rhodium, or the like, as is well known in the art.

The isatin compounds of formula (I) and (II), having a wide variety of substitutents, can be prepared by the general method illustrated in Scheme 2.

SCHEME 2

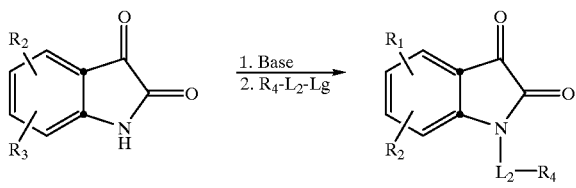

-continued

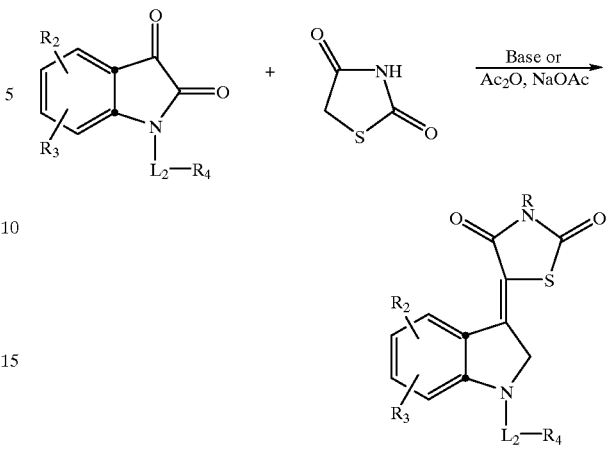

Generally, the appropriately substituted isatin compound is reacted with the $R_4$ substituent having the appropriate leaving group to give the N-alkylated isatin, followed by condensation with thiazolidinedione, as described above, to give the final product.

IV. Anti-Tumor Activity of the Telomerase Inhibitors of the Invention

The compounds of the present invention demonstrate inhibitory activity against telomerase activity in vivo, as has been and can be demonstrated as described below. The in vitro activities of the compounds of the invention can also be demonstrated using the methods described herein. As used herein, the term "ex vivo" refers to tests performed using living cells in tissue culture.

One method used to identify compounds of the invention that inhibit telomerase activity involves placing cells, tissues, or preferably a cellular extract or other preparation containing telomerase in contact with several known concentrations of a test compound in a buffer compatible with telomerase activity. The level of telomerase activity for each concentration of test compound is measured and the $IC_{50}$ (the concentration of the test compound at which the observed activity for a sample preparation was observed to fall one-half of its original or a control value) for the compound is determined using standard techniques. Other methods for determining the inhibitory concentration of a compound of the invention against telomerase can be employed as will be apparent to those of skill in the art based on the disclosure herein.

With the above-described methods, $IC_{50}$ values for several of the compounds of the present invention were determined, and found to be below 100 $\mu$M.

With respect to the treatment of malignant diseases using the compounds described herein, compounds of the present invention are expected to induce crisis in telomerase-positive cell lines. Treatment of telomerase-positive cell lines, such as HEK-293 and HeLa cells, with a compound of the invention is also expected to induce a reduction of telomere length in the treated cells.

Compounds of the invention are also expected to induce telomere reduction during cell division in human tumor cell lines, such as the ovarian tumor cell lines OVCAR-5 and SK-OV-3. Importantly, however, in normal human cells used as a control, such as BJ cells of fibroblast origin, the observed reduction in telomere length is expected to be no different from cells treated with a control substance, e.g., dimethyl sulfoxide (DMSO). The compounds of the invention also are expected to demonstrate no significant cytotoxic effects at concentrations below about 5 µM in the normal cells.

In addition, the specificity of the compounds of the present invention for telomerase can be determined by comparing their activity ($IC_{50}$) with respect to telomerase to other enzymes having similar nucleic acid binding or modifying activity similar to telomerase in vitro. Such enzymes include DNA Polymerase I, HeLa RNA Polymerase II, T3 RNA Polymerase, MMLV Reverse Transcriptase, Topoisomerase I, Topoisomerase II, Terminal Transferase and Single-Stranded DNA Binding Protein (SSB). Compounds having lower $IC_{50}$ values for telomerase as compared to the $IC_{50}$ values toward the other enzymes being screened are said to possess specificity for telomerase.

In vivo testing can also be performed using a mouse xenograft model, for example, in which OVCAR-5 tumor cells are grafted onto nude mice, in which mice treated with a compound of the invention are expected to have tumor masses that, on average, may increase for a period following the initial dosing, but will begin to shrink in mass with continuing treatment. In contrast, mice treated with a control (e.g., DMSO) are expected to have tumor masses that continue to increase.

From the foregoing those skilled in the art will appreciate that the present invention also provides methods for selecting treatment regimens involving administration of a compound of the invention. For such purposes, it may be helpful to perform a terminal restriction fragment (TRF) analysis in which DNA from tumor cells is analyzed by digestion with restriction enzymes specific for sequences other than the telomeric $(T_2 AG_3)_N$ sequence. Following digestion of the DNA, gel electrophoresis is performed to separate the restriction fragments according to size. The separated fragments are then probed with nucleic acid probes specific for telomeric sequences to determine the lengths of the terminal fragments containing the telomere DNA of the cells in the sample. By measuring the length of telomeric DNA, one can estimate how long a telomerase inhibitor should be administered and whether other methods of therapy (e.g., surgery, chemotherapy and/or radiation) should also be employed. In addition, during treatment, one can test cells to determine whether a decrease in telomere length over progressive cell divisions is occurring to demonstrate treatment efficacy.

V. Telomerase Inhibiting Compositions and Methods for Treating Diseases

The present invention also provides pharmaceutical compositions for inhibiting cell proliferation of telomerase positive cells, and treating cancer and other conditions in which inhibition of telomerase is an effective therapy. These compositions include a therapeutically effective amount of a telomerase inhibiting compound of the invention in a pharmaceutically acceptable carrier or salt.

In one embodiment, the present invention provides methods, compounds and compositions for inhibiting a telomerase enzyme, inhibiting proliferation of telomerase postive cells, and for treating cancer in a mammal. The compositions of the invention include a therapeutically effective amount of a compound of formulas I to V (or a pharmaceutically acceptable salt thereof) in a pharmaceutically acceptable carrier. The compounds and compositions of the present invention may also be used for the treatment of other telomerase mediated conditions or diseases, such as, for example, other hyperproliferative or autoimmune disorders such as psoriasis, rheumatoid arthritis, immune system disorders requiring immune system suppression, immune system reactions to poison ivy or poison oak, and the like.

In addition, it will be appreciated that therapeutic benefits for treatment of cancer can be realized by combining a telomerase inhibitor of the invention with other anti-cancer agents, including other inhibitors of telomerase such as described in U.S. Pat. Nos. 5,656,638, 5,760,062, 5,767,278, 5,770,613 and 5,863,936. The choice of such combinations will depend on various factors including, but not limited to, the type of disease, the age and general health of the patient, the aggressiveness of disease progression, the TRF length and telomerase activity of the diseased cells to be treated and the ability of the patient to tolerate the agents that comprise the combination. For example, in cases where tumor progression has reached an advanced state, it may be advisable to combine a telomerase inhibiting compound of the invention with other agents and therapeutic regimens that are effective at reducing tumor size (e.g. radiation, surgery, chemotherapy and/or hormonal treatments). In addition, in some cases it may be advisable to combine a telomerase inhibiting agent of the invention with one or more agents that treat the side effects of a disease, e.g., an analgesic, or agents effective to stimulate the patient's own immune response (e.g., colony stimulating factor).

In one such method, a pharmaceutical formulation comprises a telomerase inhibitor of the invention with an anti-angiogenesis agent, such as fumagillin, fumagillin derivatives, or AGM-1470. The latter compound is available from Takeda Chemical Industries, Ltd., while the former compounds are described in Ingber, et al., Dec. 6, 1990, "Synthetic analogues of fumagillin that inhibit angiogenesis and suppress tumor growth", Nature 348:555–557. Other combinations may include, but are not limited to, a telomerase inhibitor of the invention in addition to one or more antineoplastic agents or adjuncts (e.g., folinic acid or mesna).

Antineoplastic agents suitable for combination with the compounds of the present invention include, but are not limited to, alkylating agents including alkyl sulfonates such as busulfan, improsulfan and piposulfan; aziridines, such as a benzodizepa, carboquone, meturedepa and uredepa; ethylenimines and methylmelamines such as altretamine, triethylenemelamine, triethylenephosphoramide, triethylenethiophosphoramide and trimethylolmelamine; nitrogen mustards such as chlorambucil, chlomaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine and ranimustine. Additional agents include dacarbazine, mannomustine, mitobronitol, mitolactol and pipobroman. Still other classes of relevant agents include antibiotics, hormonal antineoplastics and antimetabolites. Yet other combinations will be apparent to those of skill in the art.

Additional agents suitable for combination with the compounds of the present invention include protein synthesis inhibitors such as abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, α-sarcin, shiga toxin, showdomycin, sparsomycin, spectinomycin, streptomycin, tetracycline, thiostrepton and trimethoprim. Inhibitors of DNA synthesis, including alkylating agents such as dimethyl sulfate, mitomycin C, nitrogen and sulfur mustards, MNNG and NMS; intercalating agents such as acridine dyes, actinomycins, adriamycin, anthracenes, benzopyrene, ethidium bromide, propidium diiodide-intertwining, and agents such as distamycin and netropsin, can also be combined with compounds of the present invention in pharmaceutical compositions. DNA base analogs such as acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxynorleucine, dideoxynucleosides, 5-fluorodeoxycytidine, 5-fluorodeoxyuridine, 5-fluorouracil, hydroxyurea and 6-mercaptopurine also can be used in combination therapies with the compounds of the invention. Topoisomerase inhibitors, such as coumermycin, nalidixic acid, novobiocin and oxolinic acid, inhibitors of cell division, including colcemide, colchicine, vinblastine and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin and streptolydigin also can be combined with the compounds of the invention to provide pharmaceutical compositions.

In another embodiment, the present invention includes compounds and compositions in which a telomerase inhibitor is either combined with or covalently bound to a cytotoxic agent bound to a targeting agent, such as a monoclonal antibody (e.g., a murine or humanized monoclonal antibody). It will be appreciated that the latter combination may allow the introduction of cytotoxic agents into cancer cells with greater specificity. Thus, the active form of the cytotoxic agent (i.e., the free form) will be present only in cells targeted by the antibody. Of course, the telomerase inhibitors of the invention may also be combined with monoclonal antibodies that have therapeutic activity against cancer.

In addition to the application of the telomerase inhibitors of the present invention to the treatment of mammalian diseases characterized by telomerase activity, telomerase inhibitors such as those disclosed herein, can be applied to agricultural phytopathogenic organisms that are characterized by telomerase activity. These organisms include nematodes such as *Ceanorhabditis elegans*, in which telomerase activity has been found, and in fungi which are expected to have telomerase activity based on the determination that the DNA of the fungus *Ustilago maydis* exhibits telomeres having the tandem TTAGGG repeats that are maintained by telomerase. Also, protozoans have TTAGGG telomeres and cause human disease. The telomerase-inhibiting compounds of the invention can be administered to plants and soil infected with phytopathogenic organisms having telomerase activity alone, or in combination with other telomerase-inhibiting agents and/or other agents used to control plant diseases. The determination of the compositions used to control such phytopathogenic organisms and the appropriate modes of delivering such compositions will be known to those having skill in the agricultural arts.

The determination that nematodes, protozoans and possibly fungi have telomerase activity also indicates that the telomerase inhibitors provided by the present invention can be used to treat nematode infections in humans and animals of veterinary interest such as dogs and cats. Nematode infection in humans and animals often is in the form of hookworm or roundworm infection and leads to a host of deadly secondary illnesses such as meningitis, myocarditis, and various neurological diseases. Thus, it will be appreciated that administration of the telomerase-inhibiting compounds such as those of the invention, alone, or in combination with other telomerase-inhibiting agents and/or other therapeutic agents, can be used to control nematode, protozoan and fungal infections in humans and animals.

In general, a suitable effective dose of a compound of the invention will be in the range of 0.001 to 1000 milligram (mg) per kilogram (kg) of body weight of the recipient per day, preferably in the range of 0.001 to 100 mg per kg of body weight per day, more preferably between about 0.1 and 100 mg per kg of body weight per day and still more preferably in the range of between 0.1 to 10 mg per kg of body weight per day. The desired dosage is preferably presented in one, two, three, four, or more subdoses administered at appropriate intervals throughout the day, or by the action of a continuous pump. These subdoses can be administered as unit dosage form, for example, containing 5 to 10,000 mg, preferably 10 to 1000 mg of active ingredient per unit dosage from. Preferably, the dosage is presented once per day at a dosing at least equal to TID, or is administered using a continuous pump delivery system.

The composition used in these therapies can be in a variety of forms. These include, for example, solid, semi-solid, and liquid dosage forms, such as tablets, pills, powders, liquid solutions or suspensions, liposomes, and injectable and infusible solutions. The preferred form depends on the intended mode of administration and therapeutic application. The compositions also preferably include conventional pharmaceutically acceptable carriers and adjuvants, as is well known to those of skill in the art. See, e.g., REMINGTON'S PHARMACEUTICAL SCIENCES, Mack Publishing Co.: Easton, Pa., 17th Ed. (1985). Preferably, administration will be by oral or parenteral (including subcutaneous, intramuscular, intravenous, and intradermal) routes. More preferably, the route of administration will be oral. The therapeutic methods and agents of this invention can of course be used concomitantly or in combination with other methods and agents for treating a particular disease or disease condition.

While it is possible to administer the active ingredient of this invention alone, it is preferable to present a therapeutic agent as part of a pharmaceutical formulation or composition. The formulations of the present invention comprise at least one telomerase activity-inhibiting compound of this invention in a therapeutically or pharmaceutically effective dose together with one or more pharmaceutically or therapeutically acceptable carriers and optionally other therapeutic ingredients. Various considerations for preparing such formulations are described, e.g., in Gilman et al. (eds.) GOODMAN AND GILMAN'S: THE PHARMACOLOGICAL BASES OF THERAPEUTICS, 8th Ed., Pergamon Press (1990); and REMINGTON'S supra. Methods for administration are discussed therein, e.g., for oral, intravenous, intraperitoneal, intramuscular, and other forms of administration. Typically, methods for administering pharmaceutical compositions will be either topical, parenteral, or oral administration methods for prophylactic and/or therapeutic treatment. Oral administration is preferred. The pharmaceutical compositions can be administered in a variety of unit dosage forms depending upon the method of administration. As noted above, unit dosage forms suitable for oral administration include powders, tablets, pills, and capsules.

One can use topical administration to deliver a compound of the invention by percutaneous passage of the drug into the systemic circulation of the patient. The skin sites include anatomic regions for transdermally administering the drug, such as the forearm, abdomen, chest, back, buttock, and mastoidal area. The compound is administered to the skin by placing on the skin either a topical formulation comprising the compound or a transdermal drug delivery device that administers the compound. In either embodiment, the delivery vehicle is designed, shaped, sized, and adapted for easy placement and comfortable retention on the skin.

A variety of transdermal drug delivery devices can be employed with the compounds of this invention. For example, a simple adhesive patch comprising a backing material and an acrylate adhesive can be prepared. The drug and any penetration enhancer can be formulated into the adhesive casting solution. The adhesive casting solution can be cast directly onto the backing material or can be applied to the skin to form an adherent coating. See, e.g., U.S. Pat. Nos. 4,310,509; 4,560,555; and 4,542,012.

In other embodiments, the compound of the invention will be delivered using a liquid reservoir system drug delivery device. These systems typically comprise a backing material, a membrane, an acrylate based adhesive, and a release liner. The membrane is sealed to the backing to form a reservoir. The drug or compound and any vehicles, enhancers, stabilizers, gelling agents, and the like are then incorporated into the reservoir. See, e.g., U.S. Pat. Nos. 4,597,961; 4,485,097; 4,608,249; 4,505,891; 3,843,480; 3,948,254; 3,948,262; 3,053,255; and 3,993,073.

Matrix patches comprising a backing, a drug/penetration enhancer matrix, a membrane, and an adhesive can also be employed to deliver a compound of the invention transdermally. The matrix material typically will comprise a polyurethane foam. The drug, any enhancers, vehicles, stabilizers, and the like are combined with the foam precursors. The foam is allowed to cure to produce a tacky, elastomeric matrix which can be directly affixed to the backing material. See, e.g., U.S. Pat. Nos. 4,542,013; 4,460,562; 4,466,953; 4,482,534; and 4,533,540.

Also included within the invention are preparations for topical application to the skin comprising a compound of the invention, typically in concentrations in the range from about 0.001% to 10%, together with a non-toxic, pharmaceutically acceptable topical carrier. These topical preparations can be prepared by combining an active ingredient according to this invention with conventional pharmaceutical diluents and carriers commonly used in topical dry, liquid, and cream formulations. Ointment and creams may, for example, be formulated with an aqueous or oily base with the addition of suitable thickening and/or gelling agents. Such bases may include water and/or an oil, such as liquid paraffin or a vegetable oil, such as peanut oil or castor oil. Thickening agents that may be used according to the nature of the base include soft paraffin, aluminum stearate, cetostearyl alcohol, propylene glycol, polyethylene glycols, woolfat, hydrogenated lanolin, beeswax, and the like.

Lotions may be formulated with an aqueous or oily base and will, in general, also include one or more of the following: stabilizing agents, emulsifying agents, dispersing agents, suspending agents, thickening agents, coloring agents, perfumes, and the like. Powders may be formed with the aid of any suitable powder base, e.g., talc, lactose, starch, and the like. Drops may be formulated with an aqueous base or non-aqueous base also comprising one or more dispersing agents, suspending agents, solubilizing agents, and the like. Topical administration of compounds of the invention may also be preferred for treating diseases such as skin cancer and fungal infections of the skin (pathogenic fungi typically express telomerase activity).

The topical pharmaceutical compositions according to this invention may also include one or more preservatives or bacteriostatic agents, e.g., methyl hydroxybenzoate, propyl hydroxybenzoate, chlorocreosol, benzalkonium chlorides, and the like. The topical pharmaceutical compositions also can contain other active ingredients such as antimicrobial agents, particularly antibiotics, anesthetics, analgesics, and antipruritic agents.

The compounds of the present invention can also be delivered through mucosal membranes. Transmucosal (i.e., sublingual, buccal, and vaginal) drug delivery provides for an efficient entry of active substances to systemic circulation and reduces immediate metabolism by the liver and intestinal wall flora. Transmucosal drug dosage forms (e.g., tablet, suppository, ointment, pessary, membrane, and powder) are typically held in contact with the mucosal membrane and disintegrate and/or dissolve rapidly to allow immediate systemic absorption. Note that certain such routes may be used even where the patient is unable to ingest a treatment composition orally. Note also that where delivery of a telomerase inhibitor of the invention would be enhanced, one can select a composition for delivery to a mucosal membrane, e.g., in cases of colon cancer one can use a suppository to deliver the telomerase inhibitor.

For delivery to the buccal or sublingual membranes, typically an oral formulation, such as a lozenge, tablet, or capsule, will be used. The method of manufacture of these formulations is known in the art, including, but not limited to, the addition of the pharmacological agent to a pre-manufactured tablet; cold compression of an inert filler, a binder, and either a pharmacological agent or a substance containing the agent (as described in U.S. Pat. No. 4,806,356); and encapsulation. Another oral formulation is one that can be applied with an adhesive, such as the cellulose derivative hydroxypropyl cellulose, to the oral mucosa, for example as described in U.S. Pat. No. 4,940,587. This buccal adhesive formulation, when applied to the buccal mucosa, allows for controlled release of the pharmacological agent into the mouth and through the buccal mucosa.

Parenteral administration is generally characterized by injection, either subcutaneously, intramuscularly, or intravenously. Thus, this invention provides compositions for intravenous administration that comprise a solution of a compound of the invention dissolved or suspended in an acceptable carrier. Injectables can be prepared in conventional forms, either as liquid solutions or suspensions, solid forms suitable for solution or suspension in liquid prior to injection, or as emulsions. Suitable excipients are, for example, water, buffered water, saline, dextrose, glycerol, ethanol, or the like. These compositions will be sterilized by conventional, well known sterilization techniques, such as sterile filtration. The resulting solutions can be packaged for use as is or lyophilized, the lyophilized preparation being combined with a sterile solution prior to administration. In addition, if desired, the pharmaceutical compositions to be administered may also contain minor amounts of non-toxic auxiliary substances, such as wetting or emulsifying agents, pH buffering agents and the like, such as for example, sodium acetate, sorbitan monolaurate, triethanolamine oleate, etc. Such formulations will be useful in treating ovarian cancers.

Another method of parenteral administration employs the implantation of a slow-release or sustained-release system, such that a constant level of dosage is maintained. See, e.g., U.S. Pat. No. 3,710,795.

Liquid pharmaceutically administrable compositions can, for example, be prepared by dissolving, dispersing, etc., an active compound as defined above and optional pharmaceutical adjuvants in an excipient, such as, for example, water, saline, aqueous dextrose, glycerol, ethanol, olive oil, and other lipophilic solvents, and the like, to form a solution or suspension. If desired, the pharmaceutical composition to be administered may also contain minor amounts of nontoxic auxiliary substances, such as wetting or emulsifying agents, pH buffering agents, and the like, for example, sodium acetate, sorbitan monolaurate, triethanolamine sodium acetate, triethanolamine oleate, etc. Actual methods of preparing such dosage forms are known and will be apparent to those skilled in this art; for example, see REMINGTON'S PHARMACEUTICAL SCIENCES, supra. The composition or formulation to be administered will contain an effective amount of an active compound of the invention.

For solid compositions, conventional nontoxic solid carriers can be used and include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 0.1–95% of active ingredient, preferably about 20%.

The compositions containing the compounds of the invention can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as a "therapeutically effective amount or dose." Amounts effective for this use will depend on the severity of the disease and the weight and general state of the patient.

In addition to internal (in vivo) administration, the compounds and compositions of the invention may be applied ex vivo to achieve therapeutic effects, as for example, in the case of a patient suffering from leukemia. In such an application, cells to be treated, e.g., blood or bone marrow cells, are removed from a patient and treated with a pharmaceutically effective amount of a compound of the invention. The cells are returned to the patient following treatment. Such a procedure can allow for exposure of cells to concentrations of therapeutic agent for longer periods or at higher concentrations than otherwise available.

Once improvement of the patient's conditions has occurred, as, for example, by the occurrence of remission in the case of a cancer patient, a maintenance dose is administered if necessary. Subsequently, the dosage or the frequency of administration, or both, can be reduced, as a function of the systems, to a level at which the improved condition is retained. When the symptoms have been alleviated to the desired level, treatment can cease. Patients can, however, require additional treatment upon any recurrence of the disease symptoms.

In prophylactic applications (e.g. chemoprevention), compositions containing the compounds of the invention are administered to a patient susceptible to or otherwise at risk of a particular disease. Such an amount is defined to be a "prophylactically effective amount or dose." In this use, the precise amounts again depend on the patient's state of health and weight.

All printed patents and publications referred to in this application are hereby incorporated herein in their entirety by this reference.

As will be apparent to those of skill in the art upon reading of this disclosure, the present invention provides valuable reagents relating to human and mammalian telomerase. The above description of necessity provides a limited and merely illustrative sampling of specific compounds, and should not be construed as limiting the scope of the invention. Other features and advantages of the invention will be apparent from the following examples and claims.

EXAMPLES

The following examples describe specific aspects of the invention to illustrate the invention and also provide a description of methods that can be used to identify and test compounds that inhibit the activity of telomerase to aid those of skill in the art in understanding and practicing the invention. The examples should not be construed as limiting the invention in any manner. Reactions were generally run on a 0.5 mmolar scale.

Example 1

Preparation of 5-benzyloxy-N-(3,4-dichlorophenyl)-3-(2,4-dioxo-thiazolidin-5-ylidene-methyl)-indole

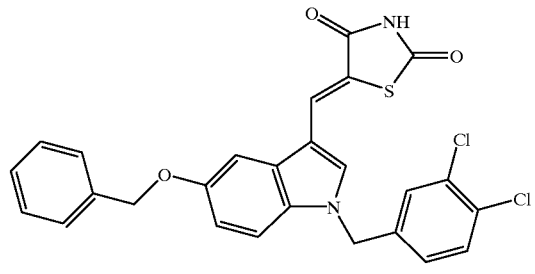

Step A. [General Procedure 1]: N-alkylation of isatins/indoles

5-Benzyloxyindole-3-carbaldehyde (0.25 g, 1 mmol), potassium carbonate (150 mg) and 3,4-dichlorobenzyl chloride (0.37 g, 1 mmol) were dissolved in DMF (10 mL) and stirred at ambient temperature. Reaction progress was determined by TLC monitoring: silica gel (1:1) EtOAc/hexanes. When the reaction was be finished (one week), the mixture was partitioned between water and EtOAc. The organic layer was washed with water (3×) and brine, dried over $Na_2SO_4$, and evaporated to a residue. The tan colored oil was dissolved in EtOAc and hexanes were added to precipitate the product, which was collected by filtration and air-dried. HPLC (uv readout at 254 nm): isocratic 35:65 $H_2O/CH_3CN$ showed greater than 95% purity 'System 1'. Identity of the title compound was confirmed by ms 411 (M+1).

Step B. [General Procedure 2]: Coupling 2,4 thiazolidinedione (TZD) to indole-aldehydes A solution of 5-benzyloxy-N-(3,4-dichlorophenyl)-indole-3-carbaldehyde (1 eq.), 2,4-thiazolidinedione (1.5 eq.) and piperidine (1.5 eq.) in EtOH was heated to 70° C. for 18 hrs. Volatiles were removed under reduced pressure and the residue was taken up in EtOAc. Addition of ether precipitated the product, which showed the appropriate mass ion and was greater than 60% pure by HPLC (uv readout at 254 nm): isocratic 35:65 $H_2O/CH_3CN$. Pure material was obtained by column chromatography on silica gel; (5:3) EtOAc/hexanes. Purity by HPLC was 85%; m\e 510 (M+1); 44% yield.

Example 2

Preparation of 5-[N-(2,6-dichlorobenzyl)-isatin-3-ylidene]-2,4-dioxo-thiazolidinedione

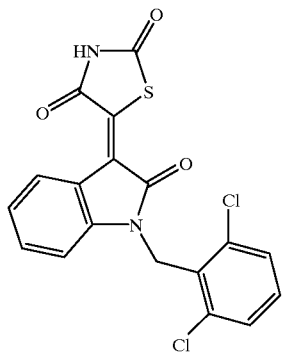

Step A: N-(2,6-dichlorobenzyl)-isatin was prepared by the method of Example 1, Step A from isatin and 2,6-dichlorobenzyl chloride.

Step B. [General Procedure 3]: Piperidine-mediated condensation of 2,4-thiazolidinedione (TZD) with isatin derivatives.

Thiazolidinedione (0.5 g, 4.2 mmol) and N-(2,6-dichlorobenzyl)isatin were suspended in DCM (10 mL), DIEA (1.4 mL) was added and the mixture was stirred at ambient temperature. After 5 min. solution was achieved. Reaction progress was monitored by NMR analysis of 100 µL aliquots from which solvent had been evaporated. After 3 days, the reaction was worked up by washing the organic layer with water (3×), drying over $Na_2SO_4$, and concentration to a foam. NMR and TLC were consistent with the formation of the title compound (0.9 g, 2.2 mmol, 70%).

Example 3

Preparation of 5-benzyloxy-3-(2,4-dioxo-thiazolidin-5-ylidenemethyl)-N-(2-thienylsulfonyl)-indole

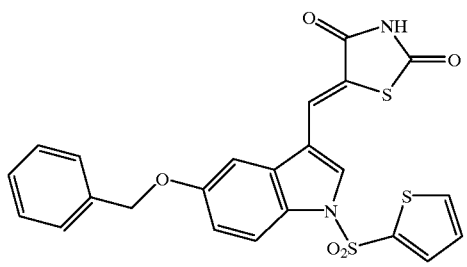

Step A: 5-Benzyloxy-3-(2,4-dioxo-thiazolidin-5-ylidenemethyl)indole was prepared by the method of Example 1, Step A from thiazolidinedione and 5-benzyloxy-indole carbaldehyde.

Step B: [General Procedure 4]: Sulfonylation of isatins/indoles.

The product from step A (50 mg) was treated with 1.2 equivalents of NaH in DMF solution with cooling for 1 hr. 2-Thienylsulfonyl chloride (34 mg, 1.3 equivaltents) was added cautiously. After 18 hrs. at ambient temperature and finally at 70° C., the mixture was poured onto ice and the precipitate was filtered. The title compound was filtered and washed with ether. HPLC 'System 1' (Ex. 1) showed 80% purity; structure confirmed by mass spec [m\e 497 (M+1)].

Example 4

Preparation of 5-[5-chloro-N-(p-tolylsulfonyl)-isatin-3-ylidene]-2,4-dioxo-thiazolidine-dione

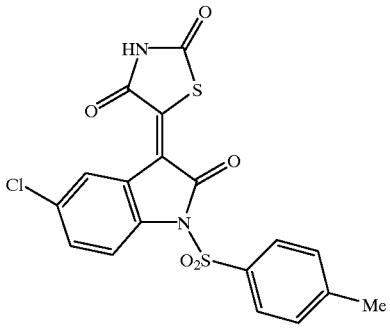

Step A. 5-chloro-N-(p-tolylsulfonyl)-isatin was prepared by the method of Example 3, Step B from 5-chloroisatin and p-tolylsulfonyl chloride.

Step B. [General Procedure 5]: Acetic acid/acetic anhydride condensation of 2,4-thiazolidinedione (TZD) with isatin/indole derivatives.

Thiazolidinedione (0.5 g, 4.2 mmol) and N-(2,6-dichlorobenzyl)isatin were suspended in DCM (10 mL), DIEA (1.4 mL) was added and the mixture was stirred at ambient temperature. After 5 min. solution was achieved. Reaction progress was monitored by NMR analysis of 100 µL aliquots from which solvent had been evaporated. After 3 days, the reaction was worked up by washing organics with water (3×), drying over $Na_2SO_4$, and concentration to a foam. NMR and TLC were consistent with the formation of the title compound (0.9 g, 2.2 mmol, 70%).

Example 5

Preparation of 5-[5-(phenylaminosulfonyl)-N-(2,6-dichlorobenzyl)isatin-3-ylidene]-thiazolidinedione

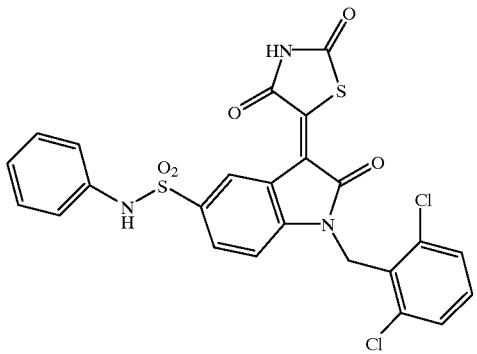

General Procedure 6: 5-(N-Substituted-sulfonamido) isatin derivatives via indole chloro-sulfonylation.

Chlorosulfonic acid (2 mL) was added carefully to of N-(2,6-dichlorobenzyl)isatin-3-ylidene thiazolidindion (a foam, 0.9 g, Example 2). The mixture was stirred at RT for 30 min, cooled in a dry ice/acetone bath and quenched by dropwise addition of water. The product was extracted with EtOAc, concentrated to a foam and triturated with hexane/EtOAc. To 10–20 mg of the acid chloride was added aniline (1 mL), a trace amount of DMAP (1 mg) and pyridine (1–2 mL). The mixture was stirred at RT for 30 min, volatiles were removed under reduced pressure and the dark residue was purified by SG chromatography (gradient elution 0–3% MeOH/DCM). NMR and ms were consistent with the formation of 5-(phenylaminosulfonyl)-N-(2,6-dichlorobenzyl) isatin-3-ylidene thiazolidinedione as the product. HPLC (System 1) showed greater than 92% purity.

Example 6

Preparation of 5-[5-chloro-N-(2-cyanoethyl)isatin-3-ylidene]-thiazolidinedione

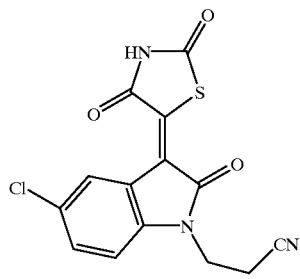

Step A. Acrylonitrile was added dropwise to a mixture of 5-chloroisatin (0.5 g) and Triton B (0.1 15 mL of a 40% solution) and stirring was continued for 48 hrs; 470 mg of an orange solid was filtered. Nmr and ms were consistent with 5-chloro-N-cyanoethyl-isatin.

Step B. The title compound was prepared by the method of Example 4, Step B.

Example 7

Preparation of 5-[5-chloro-N-(p-nitrosulfonyl)-isatin-3-ylidene]-2,4-dioxo-thiazolidine-dione

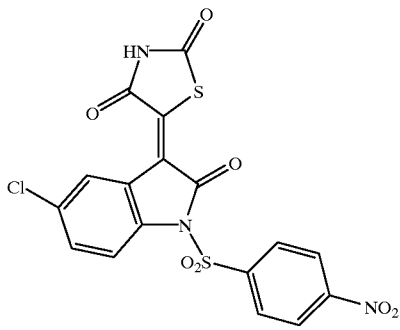

Prepared by the method of Example 4; NMR was consistent with structure; ms: m\e 466 (M+1).

Example 8

Preparation of 5-benzyloxy-N-(3,4-dichlorobenzoyl)-3-(2,4-dioxo-thiazolidin-5-ylidene-methyl)-indole

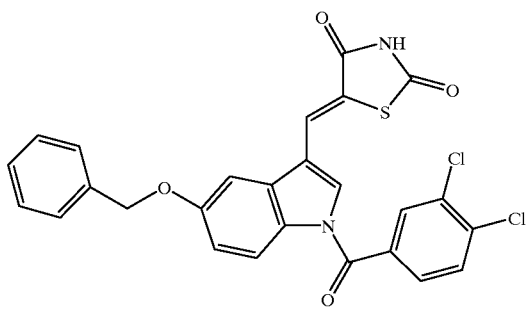

5-Benzyloxy-3-(2,4-dioxo-thiazolidin-5-ylidene-methyl)-indole (Example 1, Step A; 10 mg) was dissolved in pyridine (1.5 mL) and 3,4-dichlorobenzoyl chloride (35 mg) and a trace of dimethylaminopyridine were added. The mixture was stirred at 50–60° for 18 hrs until the reaction was determined to be complete by TLC. Volatiles were removed under reduced pressure and the residue was washed with water and ether; 10 mg; consistent nmr and ms (m\e 525 (M+1); greater than 95% by HPLC.

Example 9

Preparation of 7-benzyloxy-N-(3,4-dichlorophenyl)-3-(2,4-dioxo-thiazolidin-5-ylidene-methyl)-indole

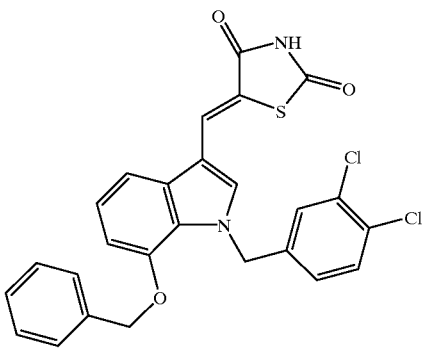

Title compound was prepared by the method of Example 1 using 7-benzyloxyindole 3-carbaldehyde (25 mg) affording the desired product (32 mg, 86% yield, greater than 95% by HPLC); nmr and ms consistent; ms: m/e 411 (M+1).

Example 10

Preparation of 5-benzyloxy-N-(3,4-dichlorophenyl)-3-(2,4-dioxo-thiazolidin-5-ylmethyl)-indole

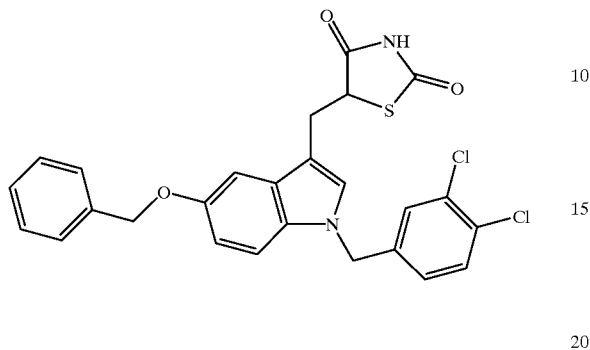

To oven-dried $SiO_2$ (150 mg) in toluene (2 mL) was added 50 mg of the thiazolidinylidene olefin (Example 1) with diethyl 1,4-dihydro-2,6-dimethyl-3,5-pyridinedicarboxylate (25 mg). The mixture was stirred and heated at 70–90° for 3 days. Mass spectral monitoring indicated the reaction was complete. Silica was filtered and washed with EtOAc and combined volatiles were removed under reduced pressure to a residue. The solid dissolved in ether and solids were filtered and discarded. Ether was evaporated and residue was washed with hexanes and air-dried to afford the reduction product; ms: m/e 512 (M+1); HPLC ~70% pure.

Example 11

Preparation of 2-(4-chlorophenyl)-N-(3,4-dichlorophenyl)-3-(2,4-dioxo-thiazolidin-5-ylidene-methyl)-indole

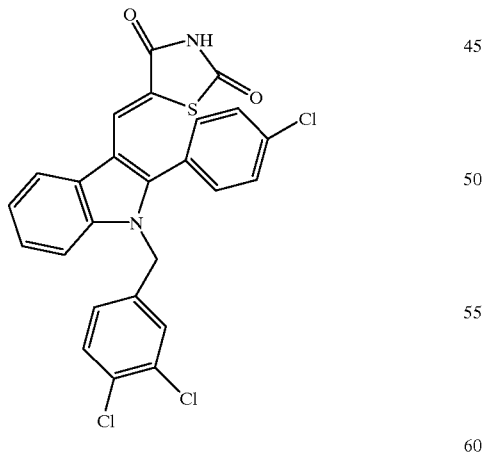

Title compound prepared by the method of Example 1 from 2-(4-chlorophenyl)-indole 3-carbaldehyde. Nmr and ms [m/e 515 (M+1)] were consistent; HPLC greater than 95% pure.

Example 12

Preparation of 5-[N-(2-(methoxycarbonyl)thien-3-ylsulfonyl)-isatin-3-ylidene]-2,4-dioxo-thiazolidine-dione

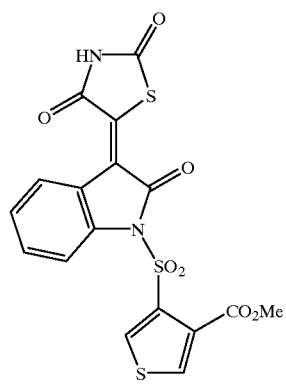

Step A: N-(2-(methoxycarbonyl)thien-3-ylsulfonyl)-isatin was prepared by General Procedure 4.

Step B: The condensation reaction was performed by General Procedure 5 to afford the title compound; ms: m/e 484 (M−1). HPLC greater than 80% purity.

Example 13

Preparation of 5-[N-(3-chlorobenzyl)-isatin-3-ylidene]-2,4-dioxo-thiazolidine-dione

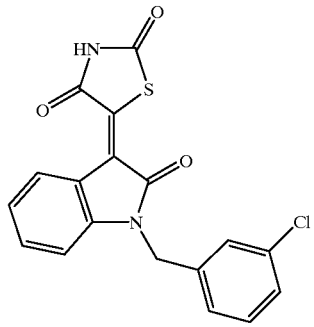

Compound was prepared by the method of Example 2; nmr and ms were consistent with the product; ms m/e 371 (M+1); HPLC showed greater than 80% purity.

Example 14

Preparation of 5-[5-chloro-N-(2,6-dichlorobenzyl)-isatin-3-ylidene]-2,4-dioxo-thiazolidine-dione

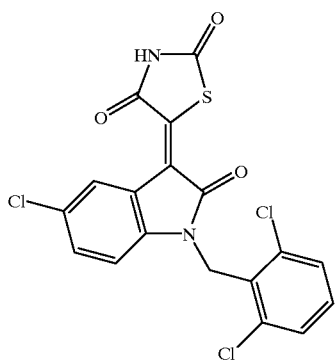

Compound was prepared by the method of Example 2; nmr and ms were consistent with the product; ms m/e 440 (M+1); HPLC showed greater than 80% purity.

Example 15

Preparation of 5-[6-chloro-N-(2,6-dichlorobenzyl)-isatin-3-ylidene]-2,4-dioxo-thiazolidine-dione

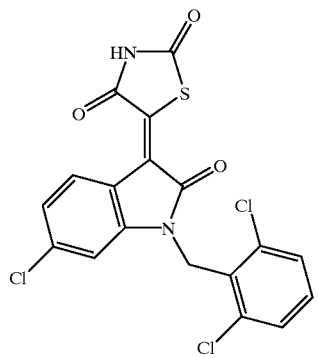

Compound was prepared by the method of Example 2; nmr and ms were consistent with the product; ms m/e 440 (M+1); HPLC showed greater than 80% purity.

Example 16

Preparation of 5-[5-methyl-N-(2,6-dichlorobenzyl)-isatin-3-ylidene]-2,4-dioxo-thiazolidine-dione

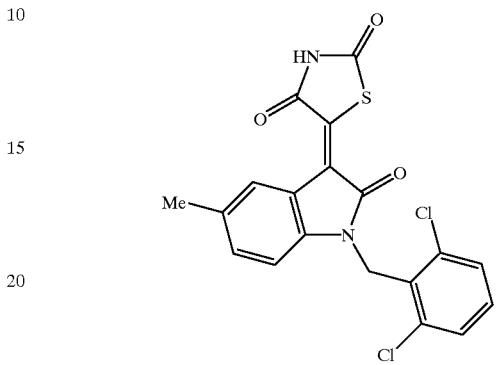

Compound was prepared by the method of Example 2; nmr and ms were consistent with the product; ms m/e 420 (M+1); HPLC showed greater than 80% purity.

Example 17

Preparation of 5-[5,6-dichloro-N-(3,4-dichlorobenzyl)-isatin-3-ylidene]-2,4-dioxo-thiazolidine-dione

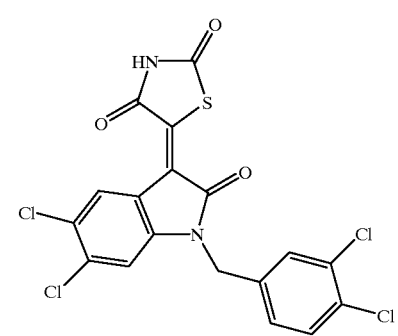

Compound was prepared by the method of Example 2; nmr and ms were consistent with the product; ms m/e 475 (M+1); HPLC showed greater than 80% purity.

Example 18

Preparation of 5-[5-chloro-N-(3-trifluoromethyl)-isatin-3-ylidene]-2,4-dioxo-thiazolidine-dione

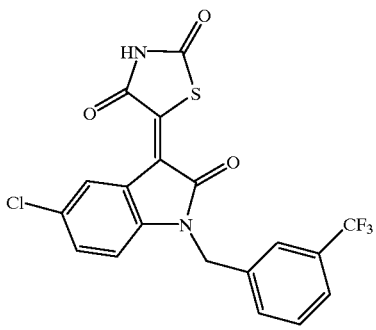

Compound was prepared by the method of Example 2; nmr and ms were consistent with the product; ms m/e 474 (M+1); HPLC showed greater than 80% purity.

Example 19

Preparation of 5-[6-benzoyl-N-(3,4-dichloro)-isatin-3-ylidene]-2,4-dioxo-thiazolidine-dione

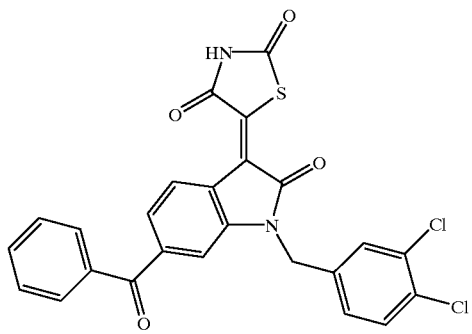

Compound was prepared by the method of Example 2; nmr and ms were consistent with the product; ms m/e 540 (M+1); HPLC showed greater than 80% purity.

Example 20

Preparation of 5-[6-benzoyl-N-(3,4-dichloro)-isatin-3-ylidene]-2,4-dioxo-thiazolidine-dione

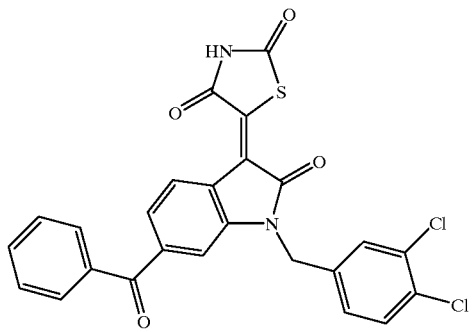

Compound was prepared by the method of Example 2; nmr and ms were consistent with the product; ms m/e 540 (M+1); HPLC showed greater than 80% purity.

Example 21

Preparation of 5-[5-(4-chlorophenylaminosulfonyl)-N-(2,6-dichlorobenzyl)isatin-3-ylidene]-thiazolidinedione

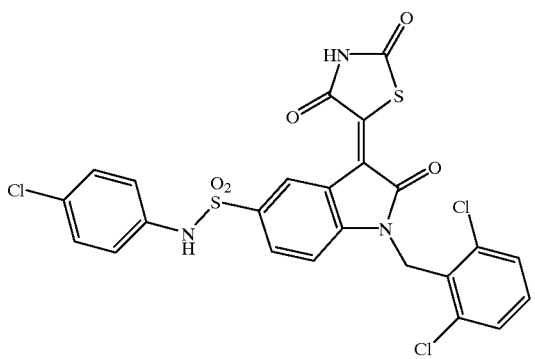

Compound was prepared by General Procedure 6; nmr and were consistent with the product; ms m/e 595 (M+1); HPLC (System 1) showed greater than 90% purity.

Example 22

Preparation of 5-[5-(4-isopropylphenylaminosulfonyl)-N-(3,4-dichlorobenzyl)isatin-3-ylidene]-thiazolidinedione

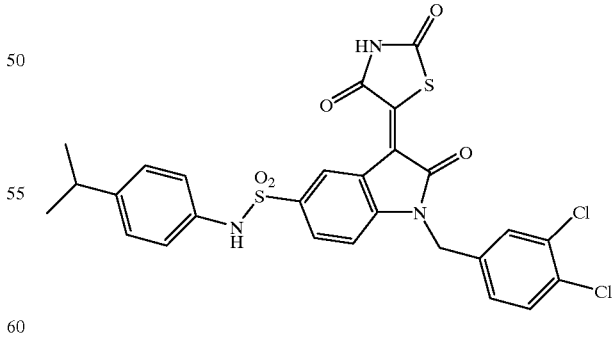

Compound was prepared by General Procedure 6; nmr and ms were consistent with the product; ms m/e 603 (M+1); HPLC (System 1) showed greater than 90% purity.

Example 23

Preparation of 5-[5-(phenylaminosulfonyl)-N-(3,4-dichlorobenzyl)isatin-3-ylidene]-thiazolidinedione

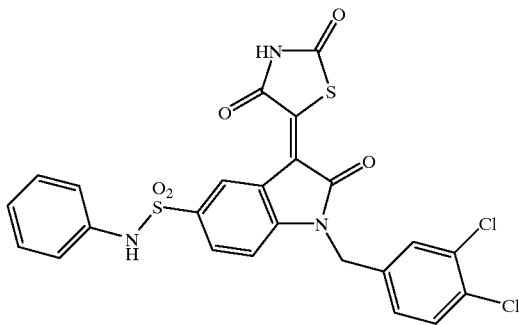

Compound was prepared by General Procedure 6; nmr and ms were consistent with the product; ms m/e 561 (M+1); HPLC (System 1) showed greater than 90% purity.

Example 24

Preparation of 5-[5-(4-trifluoromethoxyphenylaminosulfonyl)-N-(3,4-dichlorobenzyl)-isatin-3-ylidene]-thiazolidinedione

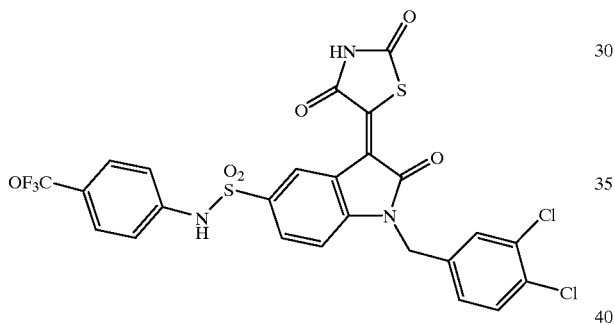

Compound was prepared by General Procedure 6; nmr and ms were consistent with the product; ms m/e 645 (M+1); HPLC (System 1) showed greater than 90% purity.

Example 25

Preparation of 5-[5-(3-trifluoromethylphenylaminosulfonyl)-N-(3,4-dichlorobenzyl)-isatin-3-ylidene]-thiazolidinedione

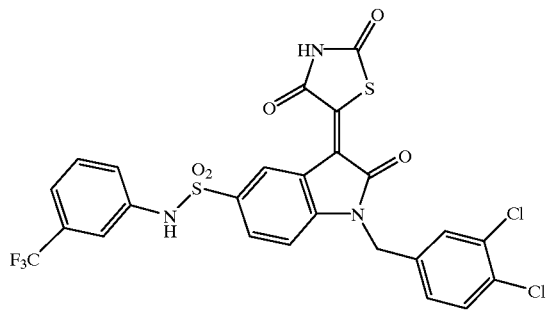

Compound was prepared by General Procedure 6; nmr and ms were consistent with the product; ms m/e 629 (M+1); HPLC (System 1) showed greater than 90% purity.

Example 26

Preparation of 5-[5-(4-ethylpiperazinylsulfonyl)-N-(3,4-dichlorobenzyl)-isatin-3-ylidene]-thiazolidinedione

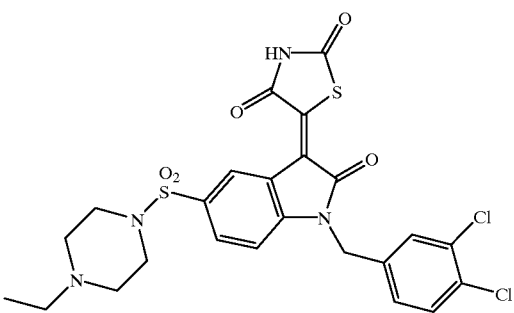

Compound was prepared by General Procedure 6; nmr and ms were consistent with the product; ms m/e 582 (M+1); HPLC (System 1) showed greater than 90% purity.

Example 27

Preparation of 5-[5-(4-methylbenzylaminosulfonyl)-N-(3,4-dichlorobenzyl)-isatin-3-ylidene]-thiazolidinedione

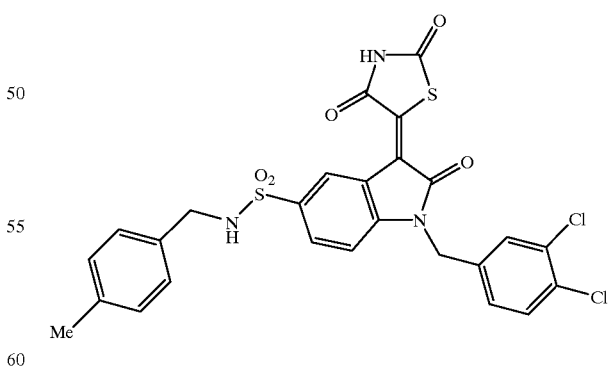

Compound was prepared by General Procedure 6; nmr and ms were consistent with the product; ms m/e 589 (M+1); HPLC (System 1) showed greater than 90% purity.

Example 28

Preparation of 5-[5-(3,4-methylenedioxybenzylaminosulfonyl)-N-(3,4-dichlorobenzyl)-isatin-3-ylidene]-thiazolidinedione

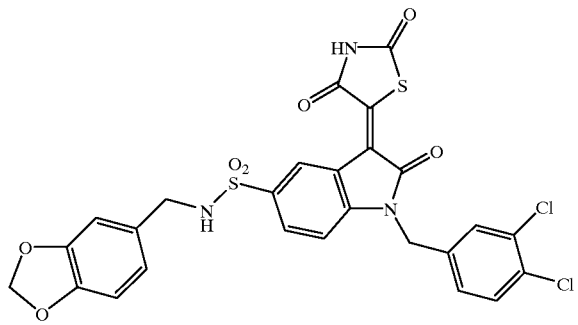

Compound was prepared by General Procedure 6; nmr and ms were consistent with the product; ms m/e 619 (M+1); HPLC (System 1) showed greater than 90% purity.

Example 29

Preparation of 5-[5-(4-phenylpiperazinylsulfonyl)-N-(3,4-dichlorobenzyl)-isatin-3-ylidene]-thiazolidinedione

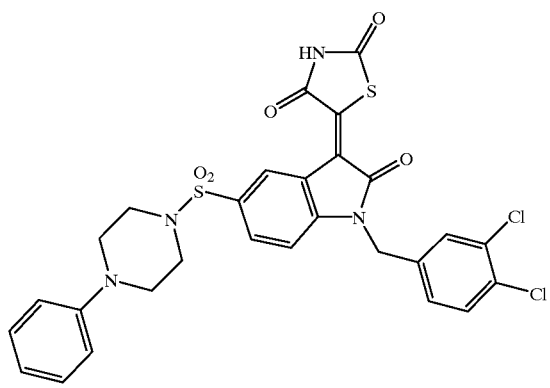

Compound was prepared by General Procedure 6; nmr and ms were consistent with the product; ms m/e 630 (M+1); HPLC (System 1) showed greater than 90% purity.

Example 30

Preparation of 5-[5-(4-morpholinophenylaminosulfonyl)-N-(3,4-dichlorobenzyl)-isatin-3-ylidene]-thiazolidinedione

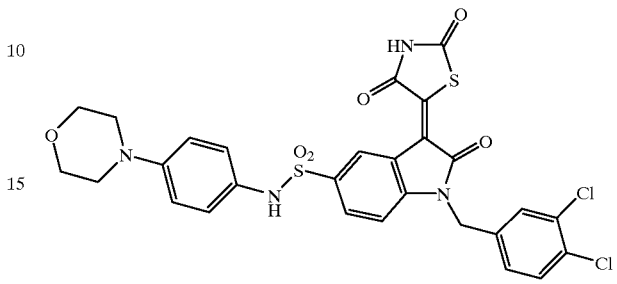

Compound was prepared by General Procedure 6; nmr and ms were consistent with the product; ms m/e 646 (M+1); HPLC (System 1) showed greater than 90% purity.

Example 31

Preparation of 5-[5-(naphth-2-ylmethylaminosulfonyl)-N-(3,4-dichlorobenzyl)-isatin-3-ylidene]-thiazolidinedione

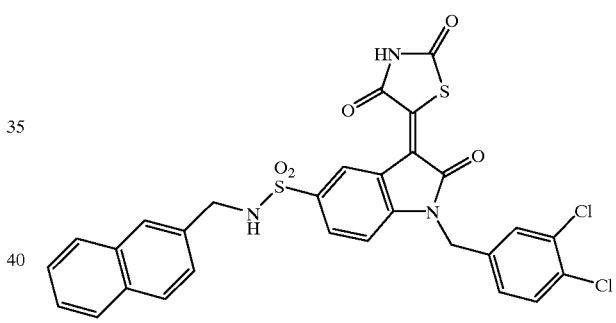

Compound was prepared by General Procedure 6; nmr and ms were consistent with the product; ms m/e 625 (M+1); HPLC (System 1) showed greater than 90% purity.

Example 32

Preparation of 5-[2-(3,4-dichlorophenyl)ethylaminosulfonyl)-N-(3,4-dichlorobenzyl)-isatin-3-ylidene]-thiazolidinedione

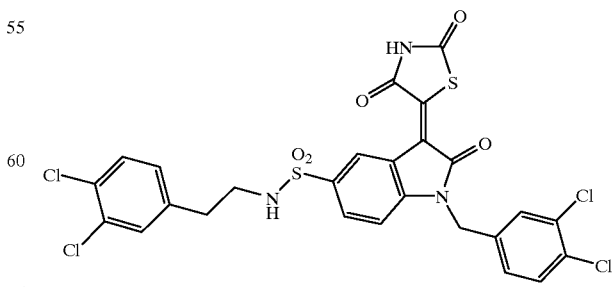

Compound was prepared by General Procedure 6; nmr and ms were consistent with the product; ms m/e 658 (M+1); HPLC (System 1) showed greater than 90% purity.

Example 33

Preparation of 5-[4-phenoxyphenylaminosulfonyl)-N-(3,4-dichlorobenzyl)-isatin-3-ylidene]-thiazolidinedione

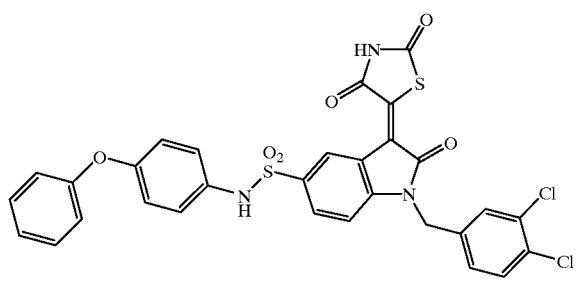

Compound was prepared by General Procedure 6; nmr and ms were consistent with the product; ms m/e 653 (M+1); HPLC (System 1) showed greater than 90% purity.

Example 34

Preparation of 5-[2-hydroxyphenylaminosulfonyl)-N-(3,4-dichlorobenzyl)-isatin-3-ylidene]-thiazolidinedione

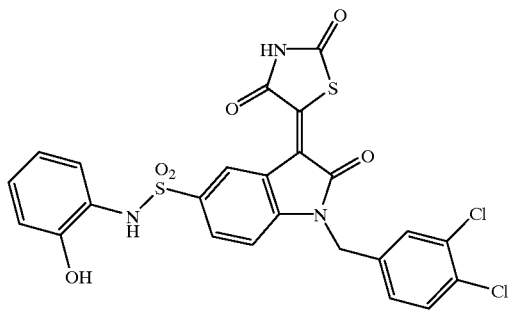

Compound was prepared by General Procedure 6; nmr and ms were consistent with the product; ms m/e 577 (M+1); HPLC (System 1) showed greater than 90% purity. Meta- and para-hydroxy derivatives were also prepared and demonstrated similar physical properties and purity.

Example 35

Preparation of 5-[6-hydroxyhexylaminosulfonyl)-N-(3,4-dichlorobenzyl)-isatin-3-ylidene]-thiazolidinedione

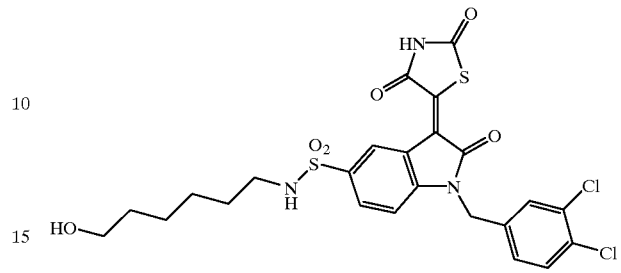

Compound was prepared by General Procedure 6; nmr and ms were consistent with the product; ms m/e 585 (M+1); HPLC (System 1) showed greater than 90% purity.

Example 36

Preparation of 5-[cyclohexylaminosulfonyl)-N-(3,4-dichlorobenzyl)-isatin-3-ylidene]-thiazolidinedione

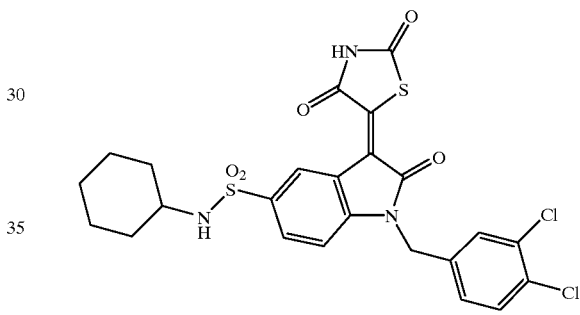

Compound was prepared by General Procedure 6; nmr and ms were consistent with the product; ms m/e 567 (M+1); HPLC (System 1) showed greater than 90% purity.

Example 37

Preparation of 5-[2-propylphenylaminosulfonyl)-N-(3,4-dichlorobenzyl)-isatin-3-ylidene]-thiazolidinedione

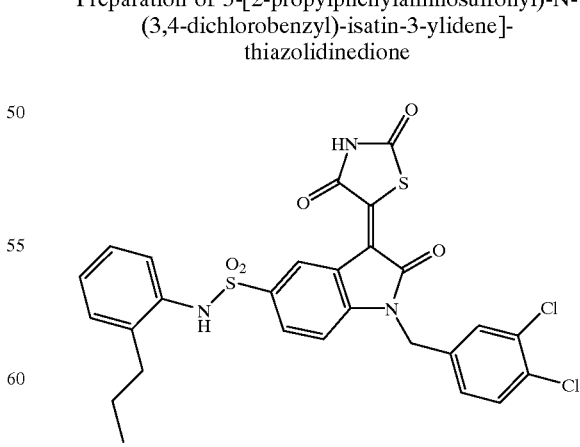

Compound was prepared by General Procedure 6; nmr and ms were consistent with the product; ms m/e 603 (M+1); HPLC (System 1) showed greater than 90% purity.

Example 38

Preparation of 5-[2,6-diisopropylphenylaminosulfonyl)-N-(3,4-dichlorobenzyl)-isatin-3-ylidene]-thiazolidinedione

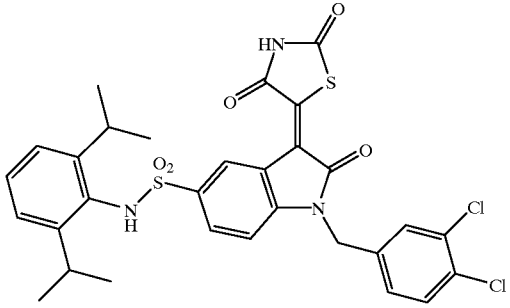

Compound was prepared by General Procedure 6; nmr and ms were consistent with the product; ms m/e 645 (M+1); HPLC (System 1) showed greater than 90% purity.

Example 39

Preparation of 5-benzyloxy-N-(2-ethoxyethyl)-3-(2,4-dioxo-thiazolidin-5-ylidene-methyl)-indole

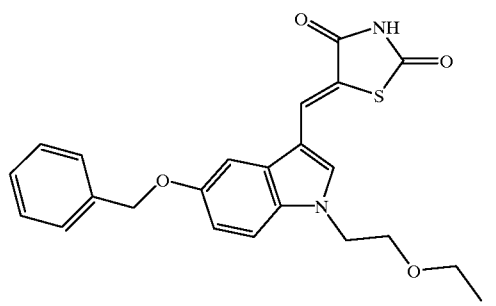

The title compound was prepared by General Procedure 1 with 5-benzyloxyindole 3-carbonitrile and 2-ethoxyethyl chloride; nmr and ms were consistent (m\e 423 (M+1); greater than 95% by HPLC.

Example 40

Preparation of 5-benzyloxy-N-(pivaloyl)-3-(2,4-dioxo-thiazolidin-5-ylidene-methyl)-indole

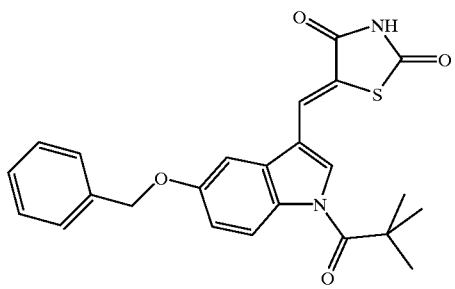

The title compound was prepared by the method of Example 8 with 5-benzyloxyindole 3-carbonitrile and piv-aloyl chloride; nmr and ms were consistent (m\e 421 (M+1); greater than 95% by HPLC.

Example 41

Preparation of 5-benzyloxy-N-(3-phenoxybenzyl)-3-(2,4-dioxo-thiazolidin-5-ylidene-methyl)-indole

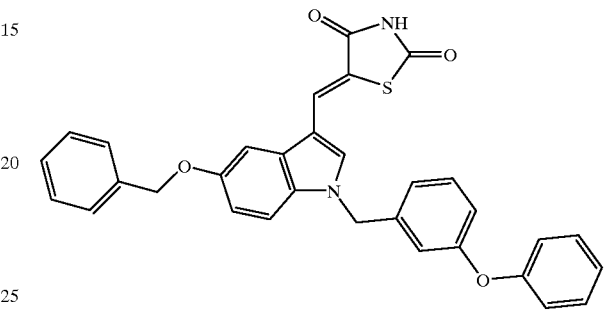

The title compound was prepared by General Procedure 1 with 5-benzyloxyindole 3-carbonitrile and 3-phenoxybenzyl chloride; nmr and ms were consistent (m\e 535 (M+1); greater than 95% by HPLC.

Example 42

Preparation of 7-benzyloxy-N-(3-phenoxybenzyl)-3-(2,4-dioxo-thiazolidin-5-ylidene-methyl)-indole

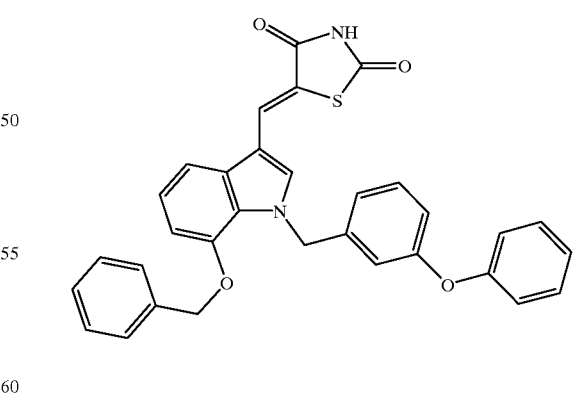

The title compound was prepared by General Procedure 1 with 7-benzyloxyindole 3-carbonitrile and 3-phenoxybenzyl chloride; nmr and ms were consistent (m\e 535 (M+1); greater than 95% by HPLC.

Example 43

Preparation of 5-methoxy-N-(3,4-dichlorobenzyl)-3-(2,4-dioxo-thiazolidin-5-ylidene-methyl)-indole

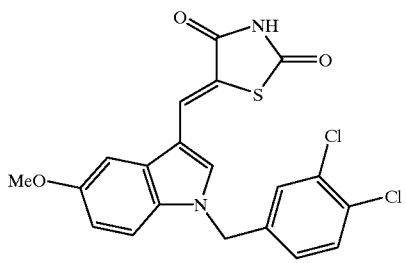

The title compound was prepared by the method of Example 1 from 5-methoxylindole 3-carbonitrile; nmr and ms were consistent (m\e 434 (M+1); greater than 95% by HPLC.

Example 44

Preparation of 5-benzyloxy-N-(3-methoxybenzoyl)-3-(2,4-dioxo-thiazolidin-5-ylidene-methyl)-indole

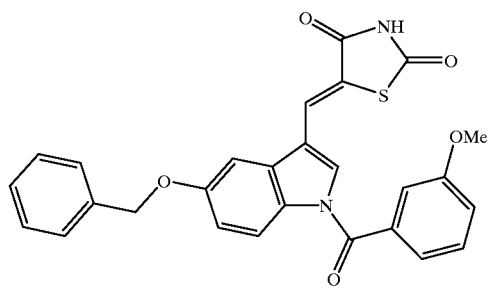

The title compound was prepared by the method of Example 8 from 5-benzyloxylindole 3-carbonitrile; nmr and ms were consistent (m\e 485 (M+1); greater than 95% purity by HPLC.

Example 45

Preparation of 5-benzyloxy-N-(4-ethoxycarbonylbenzyl)-3-(2,4-dioxo-thiazolidin-5-ylidene-methyl)-indole

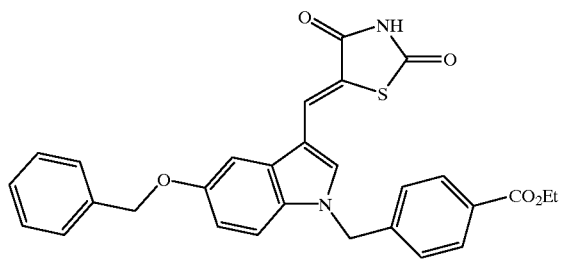

The title compound was prepared by the method of Example 1 from 5-benzyloxylindole 3-carbonitrile; nmr and ms were consistent (m\e 485 (M+1); greater than 50% purity by HPLC.

Example 46

Preparation of 5-benzyloxy-N-(4-piperidinocarbonylbenzyl)-3-(2,4-dioxo-thiazolidin-5-ylidene-methyl)-indole

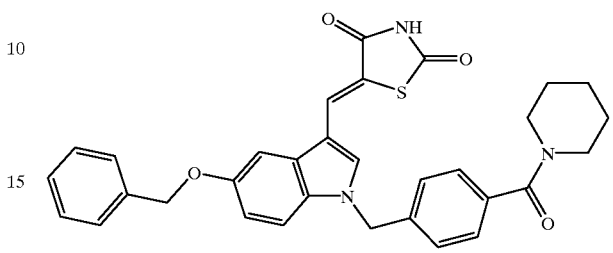

The title compound was prepared by the method of Example 1 from 5-benzyloxylindole 3-carbonitrile; nmr and ms were consistent (m\e 552 (M+1); greater than 50% purity by HPLC.

Example 47

Preparation of 5-amino-N-(3,4-dichlorobenzyl)-3-(2,4-dioxo-thiazolidin-5-ylidene-methyl)-indole

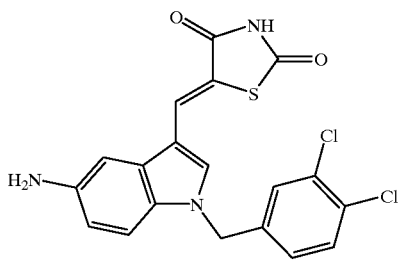

Step A. 5-Nitro-N-(3,4-dichlorobenzyl)-3-(2,4-dioxo-thiazolidin-5-ylidenemethyl)-indole was prepared by the method of Example 1 from 5-nitroindole 3-carbonitrile; nmr and ms were consistent with structure.

Step B. Reduction of the product of Step 1 was accomplished by treating 660 mg in aqueous isopropanol (1:3) containing ammonium chloride (50 mg) with iron filings (400 mg) at 60° for 18 hrs. The yellow solution was filtered and concentrated under reduced pressure. The aqueous reaction mixture was then partitioned between EtOAc and water and the organic phase washed additional water. The organic phase was dried ($Na_2SO_4$) and concentrated to a small volume whereupon a solid precipitated. This material was filtered and air dried; 440 mg (77%); nmr and ms were consistent [ms: m/e 419 (M+1)]. HPLC (System 1) showed greater than 95% purity.

Example 48

Preparation of 5-(3,4-dichlorobenzoylamino)-N-(3,4-dichlorobenzyl)-3-(2,4-dioxo-thiazolidin-5-ylidenemethyl)-indole

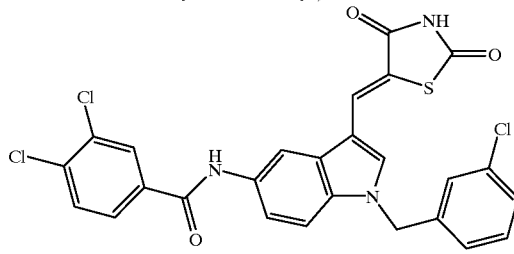

General Procedure 7: Acylation/sulfonylation of aminoindoles.

The aminoindole from Example 46 (6 mg) was dissolved in pyridine (1 mL), 2.5 mg of 3,4-dichlorobenzoyl chloride was added, and stirring was maintained for 18 hrs. The mixture was stirred at RT for 30 min, volatiles were removed under reduced pressure and the dark residue was purified by SG chromatography (gradient elution 0–3% MeOH/DCM). NMR and ms were consistent with the formation of 5-(phenylaminosulfonyl)-N-(2,6-dichlorobenzyl)isatin-3-ylidene thiazolidinedione as the product [ms: m/e 592 (M+1)]. HPLC (System 1) showed greater than 92% purity.

Example 49

Preparation of 5-[N'-(3,4-dichlorophenyl)ureido]-N-(3,4-dichlorobenzyl)-3-(2,4-dioxo-thiazolidin-5-ylidenemethyl)-indole

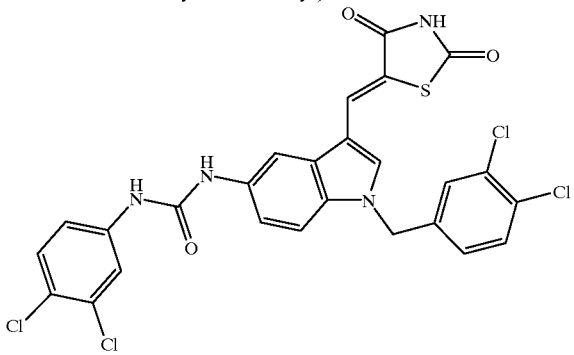

The title compound was prepared by General Procedure 7 with 3,4-dichlorophenyl isocyanate and the amino compound from Example 47 as reactants. Nmr and ms data were consistent; ms m/e 607 (M+1). HPLC (System 1): purity greater than 80%.

Example 50

Preparation of 5-[N'-(2,4-dimethoxyphenyl)ureido]-N-(3,4-dichlorobenzyl)-3-(2,4-dioxo-thiazolidin-5-ylidenemethyl)-indole

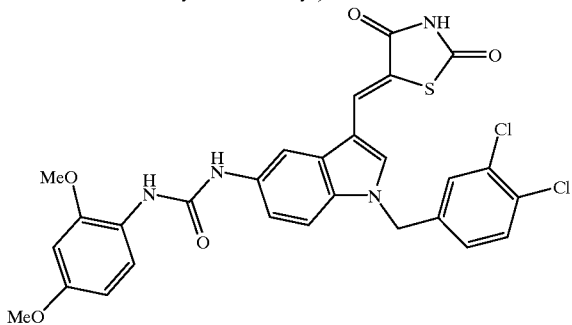

The title compound was prepared by General Procedure 7 with 2,4-dimethoxyphenyl isocyanate and the amino compound from Example 47 as reactants. Nmr and ms data were consistent; ms m/e 598 (M+1). HPLC (System 1): purity greater than 80%.

Example 51

Preparation of 5-benzoylamino-N-(3,4-dichlorobenzyl)-3-(2,4-dioxo-thiazolidin-5-ylidenemethyl)-indole

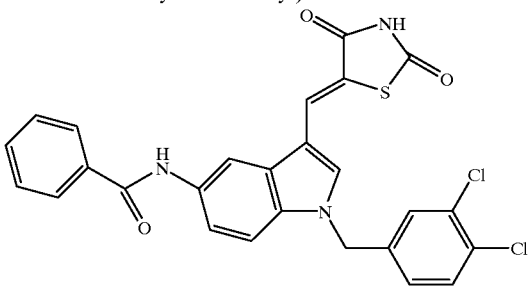

The title compound was prepared by General Procedure 7 with benzoyl chloride and the amino compound from Example 47 as reactants. Nmr and ms data were consistent; ms m/e 523 (M+1). HPLC (System 1): purity greater than 80%.

Example 52

Preparation of 5-succinamido-N-(3,4-dichlorobenzyl)-3-(2,4-dioxo-thiazolidin-5-ylidenemethyl)-indole

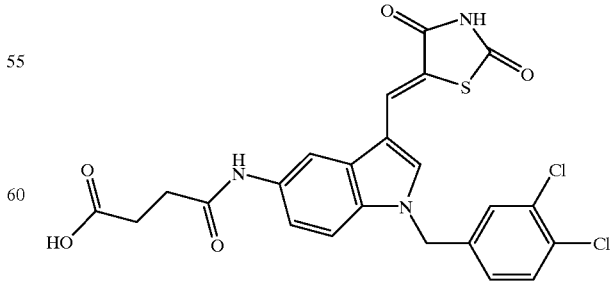

The title compound was prepared by General Procedure 7 with succinic anhydride and the amino compound from Example 47 as reactants. Nmr and ms data were consistent; ms m/e 519 (M+1). HPLC (System 1): purity greater than 80%.

Example 53

Preparation of 5-(3,4-dichlorophthalamido)-N-(3,4-dichlorobenzyl)-3-(2,4-dioxo-thiazolidin-5-ylidenemethyl)-indole

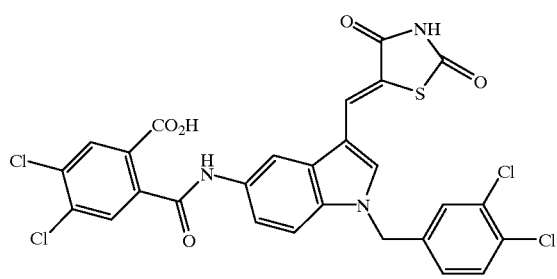

The title compound was prepared by General Procedure 7 with 3,4-dichlorophthalic anhydride and the amino compound from Example 47 as reactants. Nmr and ms data were consistent; ms m/e 636 (M+1). HPLC (System 1): purity greater than 80%.

Example 54

Preparation of 5-benzyloxy-N-[4-(2,4-dioxo-thiazolidin-5-ylidenemethyl)phenyl]-3-(2,4-dioxo-thiazolidin-5-ylidenemethyl)-indole

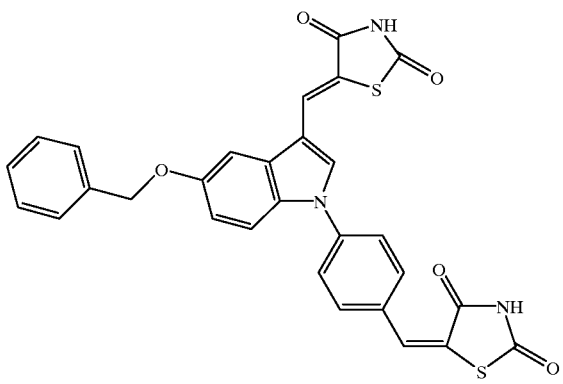

Step A: 5-Benzyloxyindole-3-carbaldehyde (0.25 g, 1 mmol), potassium carbonate (280 mg, 2 equivs.), copper II oxide (8 mg), and 4-bromobenzaldehyde (0.37 g, 2 mmol) were dissolved in DMF (10 mL) and heated at 140° for 2–3 days. Reaction progress was determined by TLC monitoring: silica gel (1:1) EtOAc/hexanes. When the reaction composition no longer changed, solids were filtered and discarded, volatiles were removed under reduced pressure, and the mixture was partitioned between water and EtOAc. The organic layer was washed with water (3×) and brine, dried over Na$_2$SO$_4$, and evaporated to a residue. Column chromatography on silica (gradient elution 0–5% MeOH/DCM) gave the dialdehyde [3,4'-(N-phenyl)]. Identity was confirmed by msj; HPLC greater than 90% purity.

Step B: Treatment of the dialdehyde with 3 equivalents of thiazolidinedione by General Procedure 2 gave the title compound. Nmr and ms [m/e 554 (M+1)] were consistent.

Example 55

Preparation of 5-methoxy-N-[4-(2,4-dioxo-thiazolidin-5-ylidenemethyl)phenyl]-3-(2,4-dioxo-thiazolidin-5-ylidenemethyl)-indole

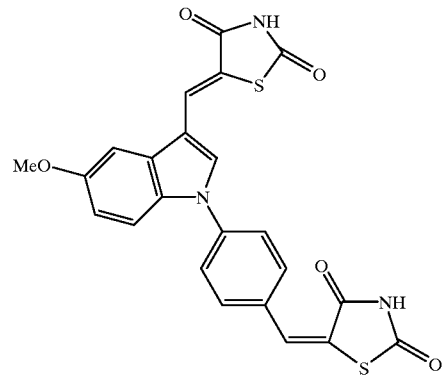

The title compound was prepared by the method of Example 54 using 5-methoxyindole 3-carbaldehyde. NMR and ms [m/e 478 (M+1)] were consistent with the product.

Example 56

Preparation of Affinity Purified Extract

Extracts used for screening telomerase inhibitors were routinely prepared from 293 cells over-expressing the protein catalytic subunit of telomerase (hTERT). These cells were found to have 2–5 fold more telomerase activity than parental 293 cells. 200 ml of packed cells (harvested from about 100 liters of culture) were resuspended in an equal volume of hypotonic buffer (10 mM Hepes pH 7.9, 1 mM MgCl$_2$, 1 mM DTT, 20 mM KCl, 1 mM PMSF) and lysed using a dounce homogenizer. The glycerol concentration was adjusted to 10% and NaCl was slowly added to give a final concentration of 0.3 M. The lysed cells were stirred for 30 min and then pelleted at 100,000×g for 1 hr. Solid ammonium sulfate was added to the S100 supernatant to reach 42% saturation. The material was centrifuged; the pellet was resuspended in one fifth of the original volume and dialyzed against Buffer 'A' containing 50 mM NaCl. After dialysis the extract was centrifuged for 30 min at 25,000×g. Prior to affinity chromatography, Triton X-100 (0.5 %), KCl (0.3 M) and tRNA (50 µg/ml) were added. Affinity oligo (5' biotinTEG-biotinTEG-biotinTEG-GTA GAC CTG TTA CCA guu agg guu ag 3'; lower case represents 2' O-methyl ribonucleotides and upper case represents deoxynucleotides) was added to the extract (1 nmol per 10 ml of extract). After an incubation of 10 min at 30° C., Neutravidin beads (Pierce; 250 µl of a 50% suspension) were added and the mixture was rotated overnight at 4° C. The beads were pelleted and washed three times with Buffer 'B' containing 0.3 M KCl, twice with Buffer 'B' containing 0.6 M KCl, and twice more with Buffer B containing 0.3 M KCl. Telomerase was eluted in Buffer 'B' containing 0.3 M KCl, 0.15% Triton X-100 and a 2.5 molar excess of displacement oligo (5'-CTA ACC CTA ACT GGT AAC AGG TCT AC-3' at 0.5 ml per 125 µl of packed Neutravidin beads) for 30 min. at room temperature. A second elution was performed and pooled with the first. Purified extracts typically had specific activities of 10 fmol nucleotides incorporated/min/µl extract, or 200 nucleotides/min/mg total protein.

| Buffer 'A" | Buffer 'B" |
| --- | --- |
| 20 mM Hepes pH 7.9 | 20 mM Hepes pH 7.9 |
| 1 mM MgCl2 | 1 mM EDTA |
| 1 mM DTT | 1 mM DTT |
| 1 mM EGTA | 10% glycerol |
| 10% glycerol | 0.5 Triton |

Example 57

Telomerase Specific Activity Determination

Three separate 100 µl telomerase assays are set up with the following buffer solutions: 50 mM Tris acetate, pH 8.2, 1 mM DTT, 1 mM EGTA, 1 mM MgCl$_2$, 100 mM K acetate, 500 µM dATP, 500 µM TTP, 10 µM $^{32}$P-dGTP (25 Ci/mmol), and a00 nM d(TTAGGG)$_3$. To the individual reactions 2.5, 5 or 10 µl of affinity-purified telomerase (see Example 56) is added and the reactions are incubated at 37° C. At 45 and 90 minutes, 40 µl aliquots are removed from each reaction and added to 160 µl of Stop Buffer (100 mM NaCl, 10 mM Na pyrophosphate, 0.2% SDS, 2 mM EDTA, 100 µg/ml tRNA). 10 µl trichloroacetic acid (TCA) (100%) is added and the sample is incubated on ice for 30 minutes. The sample is pelleted in a microcentrifuge (12000×g force) for 15 minutes. The pellet is washed with 1 ml 95% ethanol and pelleted again in the microcentrifuge (12000×g force) for 5 minutes. The pellet is resuspended in 50 µl dH$_2$O and transferred to a 12×75 glass test tube containing 2.5 ml of ice cold solution of 5% TCA and 10 mM Na pyrophosphate. The sample is incubated on ice for 30 minutes. The sample is filtered through a 2.5 cm wet (dH$_2$O) GFC membrane (S&S) on a vacuum filtration manifold. The filter is washed three times under vacuum with 5 ml ice cold 1% TCA, and once with 5 ml 95% ethanol. The filter is dried and counted in a scintillation counter using scintillation fluid. The fmol of nucleotide incorporated is determined from the specific activity of radioactive tracer. The activity of extract is calculated based on the dNTP incorporated and is expressed as fmol dNTP/min/µl extract.

Example 58

Telomerase Activity Assay

Bio-Tel FlashPlate Assay

An assay is provided for the detection and/or measurement of telomerase activity by measuring the addition of TTAGGG telomeric repeats to a biotinylated telomerase substrate primer; a reaction catalyzed by telomerase. The biotinylated products are captured in streptavidin-coated microtiter plates. An oligonucleotide probe complementary to 3.5 telomere repeats labeled with [$^{33}$P] is used for measuring telomerase products, as described below. Unbound probe is removed by washing and the amount of probe annealing to the captured telomerase products is determined by scintillation counting.

Method:
1. Compounds are stored as concentrated stocks and dissolved in 100% dimethylsulfoxide (DMSO).
2. For testing, the compounds are diluted to a 15× working stock in 50% DMSO and 2 µl is dispensed into two wells of a 96-well microtiter dish (assayed in duplicate).
3. Telomerase extract is diluted to a specific activity of 0.04–0.09 fmol dNTP incorporated/min./µl in Telomerase Dilution Buffer and 18 µl added to each sample well to preincubate with compound for 30 minutes at room temperature.
4. The telomerase reaction is initiated by addition of 10 µl Master Mix to the wells containing telomerase extract and compound. The plates are sealed and incubated at 37° C. for 90 min.
5. The reaction is stopped by the addition of 10 µl HCS.
6. 25 µl of the reaction mixture is transferred to a 96-well streptavidin-coated FlashPlate (NEN) and incubated for 2 hours at room temperature with mild agitation.
7. The wells are washed three times with 180 µl 2×SSC without any incubation.
8. The counts of probe annealed to biotinylated telomerase products are detected on a scintillation counter.

Buffers:
Telomerase Dilution Buffer
50 mM Tris-acetate, pH 8.2
1 mM DTT
1 mM EGTA
1 mM MgCl$_2$
830 nM BSA
Master Mix (MM)
50 mM Tris-acetate, pH 8.2
1 mM DTT
1 mM EGTA
1 mM MgCl$_2$
150 mM K acetate
10 µM dATP
20 µM dGTP
120 µM dTTP
100 nM biotinylated primer (5'-biotin-AATCCGTCGAGCAGAGTT-3')
5.4 nM labeled probe [5'-CCCTAACCCTAACCCTAACCC-($^{33}$P) A$_{1-50}$-3']; specific activity approximately $10^9$ cpm/µg or higher
Hybridization Capture Solution (HCS)
12×SSC (1×–150 mM NaCl/30 mM Na$_3$Citrate)
40 mM EDTA
40 mM Tris-HCl, pH 7.0

Using the foregoing assay, the compounds of Examples 1–55 were shown to have telomerase IC$_{50}$ values below 100 µM.

Example 59

Anti-tumor Activity

Ex vivo Studies a. Reduction of Telomere Length in Tumor Cells

Colonies of the tumor cell lines, such as the ovarian tumor cell lines OVCAR-5 and SK-OV-3, and normal human cells used as a control (e.g., normal human BJ cells) are prepared using standard methods and materials. In one test, the colonies are prepared by seeding 15-centimeter dishes with about $10^6$ cells in each dish. The dishes are incubated to allow the cell colonies to grow to about 80% confluence, at which time each of the colonies are divided into two groups. One group is exposed to a subacute dose of a compound of the invention at a predetermined concentration (e.g., between about 5 µM and about 20 µM) for a period of about 4–8 hours after plating following the split; the other group is exposed to a control (e.g., DMSO).

Each group is then allowed to continue to divide, and the groups are split evenly again (near confluence). The same number of cells are seeded for continued growth. The compound or control is added every fourth day to the samples at the same concentration delivered initially. Remaining cells are analyzed for telomere length. As the untested cell cultures near confluence, the samples are split again as just described. This sequence of cell doubling and splitting is continued for about 20 to 25 doublings. Thus, a determination of telomere length as a function of cell doublings is obtained.

Telomere length is determined by digesting the DNA of the cells using restriction enzymes specific for sequences other than the repetitive $T_2 AG_3$ sequence of human telomeres (TRF analysis). The digested DNA is separated by size using standard techniques of gel electrophoresis to determine the lengths of the telomeric repeats, which appear, after probing with a telomere DNA probe, on the gel as a smear of high-molecular weight DNA (approximately 2 Kb–15 Kb).

The results of the telomere length analysis are expected to indicate that the compounds of the invention have no effect on the rate of decrease in telomere length for control cells as a function of progressive cell doublings. With respect to the tumor cell lines, however, measurable decreases in telomere length are expected to be determined for tumor cells exposed to the compounds of the invention. Thus, the compounds of the invention are expected to cause resumption of the normal loss of telomere length as a function of cell division in tumor cells. Tumor cells exposed to the control are expected to maintain steady telomere lengths.

In another experiment, HEK-293 cells are incubated with a compound of the invention and a control at concentrations between about 1 $\mu$M and about 20 $\mu$M using the protocol just described. Cells are expected to enter crisis (i.e., the cessation of cell function) within several weeks following administration of the test compound of the invention. In addition, TRF analysis of the cells using standard methodology is expected to show that the test compounds of the invention are effective in reducing telomere length. In addition to the HEK-293 cells described above, this assay can be performed with any telomerase-positive cell line, such as HeLa cells.

b. Specificity

Compounds of the invention are screened for activity ($IC_{50}$) against telomerase and several enzymes having nucleic acid binding or modifying activities related to telomerase using standard techniques. The enzymes being screened include Telomerase, DNA Polymerase I, HeLa RNA Polymerase II, T3 RNA Polymerase, MMLV Reverse Transcriptase, Topoisomerase I, Topoisomerase II, Terminal Transferase and Single-Stranded DNA Binding Protein (SSB). The specificity of a compound of the invention for telomerase is determined by comparing the $IC_{50}$ of the compound with respect to telomerase with the $IC_{50}$ values of the compound for each of the enzymes being screened. The compound is determined to have specificity for telomerase if the $IC_{50}$ for telomerase of the compound is lower than the $IC_{50}$ values for each of the other enzymes being screened.

While the preferred embodiment of the invention has been illustrated and described, it will be appreciated that various changes can be made therein without departing from the spirit and scope of the invention.

We claim:

1. A compound of formula (I):

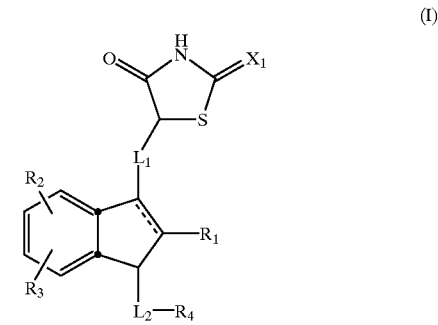

wherein $X_1$ is chosen from O, S, $CH_2$, or $NR_5$ where $R_5$ is H, lower alkyl or aryl;

$L_1$ is a direct single bond, —$CH_2$—, or —CH=;

⇌ is a single or a double bond;

$R_1$ is selected from the group consisting of H, $OR_5$, $SR_5$, $CR_6R_7R_8$, and oxo only when ⇌ is a single bond, wherein $R_6$, $R_7$, and $R_8$ are independently selected from H, OH, lower alkyl, aryl, or heteroaryl;

$R_2$ and $R_3$ are independently selected from the group consisting of H, OH, halogen, mercapto, nitro, cyano, trifluromethyl, lower alkyl, lower alkoxy, aryloxy, $NR_9R_{10}$, $SO_2NR_9R_{10}$, $OCHR_9R_{10}$, $COR_9$, $CO_2R_9$, $NHCONHR_9$, $CONHR_9$, $NHCOR_9$, aryl, and heteroaryl wherein $R_9$ and $R_{10}$ are independently selected from the group consisting of hydrogen, lower alkyl, aryl, and heteroaryl, and $R_2$ and $R_3$ further represent replacement in the ring of ring methine (—CH=) atoms with aza (—N=) atoms;

$L_2$ is a direct single bond or a linking group having from 1 to 3 atoms independently selected from unsubstituted or substituted carbon, N, O or S; and $R_4$ is H, lower alkyl, alkaryl, aryl, or heteroaryl;

or a pharmaceutically acceptable salt thereof, with the proviso that when $X_1$ is O, $R_1$ is Me, $L_2$ is a direct single bond, and $R_4$ is H or Me, then $R_2$ and $R_3$ are not OMe, and when $X_1$ is S, $L_1$ is —CH=; ⇌ is a double bond, $R_1$ is H, $L_2$ is a direct single bond, and $R_4$ is H, then $R_2$ and $R_3$ are not H or F.

2. A compound of claim 1, wherein ⇌ is a single bond, and $R_1$ is H or oxo.

3. A compound of claim 1, wherein $R_2$ and $R_3$ are halogen.

4. A compound of claim 3, wherein the halogen is Cl.

5. A compound of claim 1, wherein $R_3$ is hydrogen.

6. A compound of claim 5, wherein $R_2$ is halogen.

7. A compound of claim 6, wherein the halogen is Cl.

8. A compound of claim 6, wherein $R_2$ is 4-Cl, 5-Cl, or 6-Cl.

9. A compound of claim 8, wherein $R_2$ is 4-Cl.

10. A compound of claim 5, wherein $R_2$ is $SO_2NHR_9$.

11. A compound of claim 10, wherein $R_9$ is aryl.

12. A compound of claim 10, wherein $R_9$ is alkyl.

13. A compound of claim 5, wherein $R_2$ is $COR_9$.

14. A compound of claim 12, wherein $R_9$ is aryl.

15. A compound of claim 1, wherein $L_2$ is a direct bond.

16. A compound of claim 1, wherein $L_2$ is selected from the group consisting of —O—, —S—, —SO—, —$SO_2$—, —NH—, —$(CH_2)_n$—, —$(OCH_2)_n$—, —$(CH_2)_nO(CH_2)_m$—, —SCH₂—, —OC(O)—, —C(O)NH—, —OC(O)CH₂—, —OC(O)NH—, —NHC(O)—, and —NHC(O)NH—, where n and m are independently selected from an integer between 0 and 1.

17. A compound of claim 16, wherein L₂ is —CH₂—.
18. A compound of claim 16, wherein L₂ is —SO₂—.
19. A compound of formula (II):

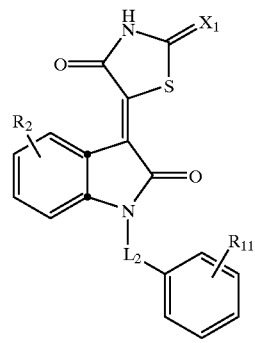

(II)

wherein X₁ is O or S;
R₂ is H, OH, halogen, lower alkyl, aryl, or heteroaryl;
L₂ is a direct bond, CH₂, or SO₂; and
R₁₁ is H, halogen or lower alkoxy;
or a pharmaceutically acceptable salt thereof.

20. A compound of claim 19, wherein X₁ is O, L₂ is CH₂, and R₂ and R₁₁ are chloro.

21. A method of inhibiting a telomerase enzyme comprising contacting the enzyme with a compound of compound 1.

22. A method of inhibiting a telomerase enzyme comprising contacting the enzyme with a compound of compound 1.

23. A method of inhibiting proliferation of a telomerase positive cell comprising contacting the cell with a compound of claim 1.

24. The method of claim 23, wherein the cell is a mammalian cell.

25. The method of claim 24, wherein the cell is a human cell.

26. The method of claim 25, wherein the cell is a cancer cell.

27. A method of treating a tumor comprising contacting the tumor with a compound of claim 1.

28. A method of treating a tumor comprising contacting the tumor with a compound of claims 19.

29. A pharmaceutical composition comprising a pharmaceutically effective amount of a compound of claim 1 and a pharmaceutically acceptable carrier.

30. A pharmaceutical composition comprising a pharmaceutically effective amount of a compound of claim 19 and a pharmaceutically acceptable carrier.

* * * * *